United States Patent [19]
Klagsbrun et al.

[11] Patent Number: 5,811,393
[45] Date of Patent: Sep. 22, 1998

[54] HEPARIN BINDING MITOGEN WITH HOMOLOGY TO EPIDERMAL GROWTH FACTOR (EGF)

[75] Inventors: Michael Klagsbrun, Newton, Mass.; Judith A. Abraham, San Jose, Calif.; Shigeki Higashiyama, Osaka, Japan; Gail E. Besner, Buffalo, N.Y.

[73] Assignees: The Childrens Medical Center Corp., Boston, Mass.; Scios Nova, Inc., Mountain View, Calif.

[21] Appl. No.: 39,364

[22] PCT Filed: Oct. 16, 1991

[86] PCT No.: PCT/US91/07691

§ 371 Date: Jun. 15, 1993

§ 102(e) Date: Jun. 15, 1993

Related U.S. Application Data

[63] Continuation-in-part of Ser. No. 598,082, Oct. 16, 1990, abandoned.

[51] Int. Cl.$^6$ .......................... C12N 15/18; A61K 38/18; C07K 14/475
[52] U.S. Cl. .......................... 514/12; 536/23.5; 435/69.1; 435/320.1; 435/325; 530/350; 530/399; 530/324
[58] Field of Search .............................. 435/6, 69.1, 69.4, 435/240.2, 252.3, 320.1, 172.3, 325; 530/324, 350, 399; 536/23.5; 514/2, 12

[56] References Cited

FOREIGN PATENT DOCUMENTS

| 3902157 | 7/1989 | Germany . |
| 2 216 185 | 8/1989 | United Kingdom . |

OTHER PUBLICATIONS

Besner, G. et al., Cell Regulation, 1:811–19, Oct. 1990.
Besner, G. et al., J. Cell Biology, 6 (Part 3): 481a, abstract 2706, 1988 (29 Jan.–2 Feb. 1989 meeting).
Lupu et al., Science, 269:1552–1555, 1990, "Direct Interaction of a ligand for the erb82 Oncogene Product with the EGF Receptor and p185$^{erb82}$."
Madtas et al., Cell, 53:285–283, 1988, "Induction of Transforming Growth Factor–α in Activated Human Alveolar Macrophages."
Assoian et al., Proc. Natl. Acad. Sci., 84:6020–6024, 1987, "Expression and Secretion of type β Transforming Growth Factor by Activated Human Macrophages."
Hazuda et al., The Journal of Biological Chemistry, 263:8473–8479, 1988, "The Kinetics of Interlukin 1 Secretion form Activated Monocytes."
Schmidt et al., The Journal of Clinical Investigation, Inc., 73:1462–1472, 1984, "Silicon–stimulated Monocytes Release Fibroblast Proliferation Factors Identical to Interleukin 1."
Leibovich, Nature, 329:630–632, 1987, "Macrophage–induced angiogenesis is mediated by tumour necrosis factor–α."
Singh et al., Proc. Nat'l Acad. Sci, 85:6374–6378, 1988, "Purification and biochemical properties of a human monocyte–derived growth factor."
Nathan, Journal of Clinical Investigation, 79:319–326, 1987, "Secretory Products of Macrophages."
Van Brunt and Klausner, Biotechnology, 6:25–30, 1988, "Growth Factors Speed Wound Healing."
Agel et al., J. Pathol., 146:197–204, 1985, "Identification of Macrophages and Smooth Muscle Cells in Human Atherosclerosis Using Monoclonal Antibodies."
Folkman and Klagsbrun, Science 235:397–442, 1987, "Angiogenic Factors."
Lobb et al., J. Biol. Chem., 261:1924–1928, 1986, "Purification and Characterization of Heparin–binding Endothelial Cell Growth Factors."
Rubin et al. Proc. Natl. Acad. Sci. USA, 86:802–806, 1989, "Pufification and characterization of newly identified growth factor specific for epithelial cells."
Gospodarowicz et al., Proc. Natl. Sci. USA, 81:6963–6967, 1984, "Isolation of brain fibroblast growth factor by heparin–Sepharose affinity chromatography: Identity with pituitary fibroblast growth factor."
Shing et al., J. Cell Biochem. 29:275–287, 1985, "Angiogenesis Is Stimulated by a Tumor–Derived Endothelial Cell Growth Factor."
Bōhlen et al., Febs Lett., 185:177–181, 1985, "Human brain fibroblast growth factor."
Shing et al., Science, 223:1296–1298, 1984, "Heparin Affinity: Purification of a Tumor–Derived Capillary Endothelial Cell Growth Factor."
Shoyab et al., Science, 243: 1074–1076, 1989, "Structure and Function of Human Amphiregulin: A Member of the Epidermal Growth Factor Family."
Derynck et al., Cell, 38:287–297, 1984, "Human Transforming Growth Factor–α: Precursor Structure and Expression in E. coli."
Gregory, Nature, 257:325–327, 1975, "Isolation and structure of urogastrone and its relationship to epidermal growth factor."
Suggs et al., Proc. Natl. Acad. Sci. USA, 78:6613–6617, 1981, "Use of synthetic oligonucleotides as hybridization probes: Isolation of cloned cDNA sequences for human $\beta_2$–microglobulin."

*Primary Examiner*—Marianne P. Allen
*Attorney, Agent, or Firm*—Fish & Richardson P.C.

[57] ABSTRACT

Disclosed are heparin binding mitogens which include an epidermal growth factor-homologous segment (HB-EHM). These factors stimulate proliferation of fibroblast cells, epithelial cells, and smooth muscle cells, but not endothelial cells. Also disclosed are isolated antibodies that recognize, and purified nucleic acids that encode, the above growth factors as well as isolated polypeptides, vectors containing such nucleic acids, and cells harboring such vectors. Growth factors of this invention may be used for accelerating the rate of wound healing, for the in vitro culture of HB-EHM-responsive cells, and for the identification of antagonists to HB-EHM.

24 Claims, 5 Drawing Sheets

```
GCACTGGCCACACCAAACAAGGAGGAGCACGGGAAAAGAAAGAAGAAA
 A  L  A  T  P  N  K  E  E  H  G  K  R  K  K  K
                         90

GGCAAGGGGCTAGGGAAGAAGAGAGGGACCCATGTCTTCGGAAATACAAGGACTTCTGCATCCATGGAGAA
 G  K  G  L  G  K  K  R  D  P  C  L  R  K  Y  K  D  F  C  I  H  G  E
                    100                          110                  120

TGCAAATATGTGAAGGAGCTCCGGGCTCCCTCCTGCATCTGCCACCCGGGTTACCATGGAGAGAGGTGT
 C  K  Y  V  K  E  L  R  A  P  S  C  I  C  H  P  G  Y  H  G  E  R  C
                         130                          140

CATGGGCTGAGC
 H  G  L  S
```

```
   1 GCTACGCGGGCCACGCTGCTGGCTGGCCTGACCTAGGCGCGCGGGGTCGGGCGGCCGCGCGGGCGGGCT
  70 GAGTGAGCAAGACAAGACACTCAAGAAGAGCGAGCTGCGCCTGGGTCCCGGCCAGGCTTGCACGCAGAG
 139 GCGGGCGGCAGACGGTGCCCGGCGGAATCTCCTGAGCTCCGCCGCCCAGCTCTGGTGCCAGCGCCCAGT
 208 GGCCGCCGCTTCGAAAGTGACTGGTGCCTCGCCGCCTCCTCGGTGCGGGACCATGAAGCTGCTGCCG
                                                         M   K   L   L   P
                                                         1

277 TCGGTGGTGCTGAAGCTCTTTCTGGCTGCAGTTCTCTCGGCACTGGTGACTGGCGAGAGCCTGGAGCGG
     S   V   V   L   K   L   F   L   A   A   V   L   S   A   L   V   T   G   E   S   L   E   R
                     10                                  20

346 CTTCGGAGAGGGCTAGCTGCTGGAACCAGCAACCCGGACCCTCCCACTGTATCCACGGACCAGCTGCTA
     L   R   R   G   L   A   A   G   T   S   N   P   D   P   P   T   V   S   T   D   Q   L   L
             30                                  40                                  50

415 CCCCTAGGAGGCGGCCGGGACCGGAAAGTCCGTGACTTGCAAGAGGCAGATCTGGACCTTTTGAGAGTC
     P   L   G   G   G   R   D   R   K   V   R   D   L   Q   E   A   D   L   D   L   L   R   V
                                     60                                  70

484 ACTTTATCCTCCAAGCCACAAGCACTGGCCACACCAAACAAGGAGGAGCACGGGAAAAGAAAGAAGAAA
     T   L   S   S   K   P   Q   A   L   A   T   P   N   K   E   E   H   G   K   R   K   K   K
                             80                                  90

553 GGCAAGGGGCTAGGGAAGAAGAGGGACCCATGTCTTCGGAAATACAAGGACTTCTGCATCCATGGAGAA
     G   K   G   L   G   K   K   R   D   P   C   L   R   K   Y   K   D   F   C   I   H   G   E
                     100                                 110                                 120

622 TGCAAATATGTGAAGGAGCTCCGGGCTCCCTCCTGCATCTGCCACCCGGGTTACCATGGAGAGAGGTGT
     C   K   Y   V   K   E   L   R   A   P   S   C   I   C   H   P   G   Y   H   G   E   R   C
                                     130                                 140

691 CATGGGCTGAGCCTCCCAGTGGAAAATCGCTTATATACCTATGACCACACAACCATCCTGGCCGTGGTG
     H   G   L   S   L   P   V   E   N   R   L   Y   T   Y   D   H   T   T   I   L   A   V   V
                             150                                 160

760 GCTGTGGTGCTGTCATCTGTCTGTCTGCTGGTCATCGTGGGCTTCTCATGTTTAGGTACCATAGGAGA
     A   V   V   L   S   S   V   C   L   L   V   I   V   G   L   L   M   F   R   Y   H   R   R
                     170                                 180

829 GGAGGTTATGATGTGGAAAATGAAGAGAAAGTGAAGTTGGGCATGACTAATTCCCACTGAGAGAGACTT
     G   G   Y   D   V   E   N   E   E   K   V   K   L   G   M   T   N   S   H
                                     190                                 200

898 GTGCTCAAGGAATCGGCTGGGGACTGCTACCTCTGAGAAGACACAAGGTGATTTCAGACTGCAGAGGGG
 967 AAAGACTTCCATCTAGTCACAAAGACTCCTTCGTCCCCAGTTGCCGTCTAGGATTGGGCCTCCCATAAT
1036 TGCTTTGCCAAAATACCAGAGCCTTCAAGTGCCAAACAGAGTATGTCCGATGGTATCTGGGTAAGAAGA
1105 AAGCAAAAGCAAGGGACCTTCATGCCCTTCTGATTCCCCTCCACCAAACCCCACTTCCCCTCATAAGTT
1174 TGTTTAAACACTTATCTTCTGGATTAGAATGCCGGTTAAATTCCATATGCTCCAGGATCTTTGACTGAA
1243 AAAAAAAAAGAAGAAGAAGGAGAGCAAGAAGGAAAGATTTGTGAACTGGAAGAAAGCAACAAAGAT
1312 TGAGAAGCCATGTACTCAAGTACCACCAAGGGATCTGCCATTGGGACCCTCCAGTGCTGGATTTGATGA
1381 GTTAACTGTGAAATACCACAAGCCTGAGAACTGAATTTTGGGACTTCTACCCAGATGGAAAAATAACAA
1450 CTATTTTTGTTGTTGTTGTTTGTAAATGCCTCTTAAATTATATATTTATTTTATTCTATGTATGTTAAT
1519 TTATTTAGTTTTTAACAATCTAACAATAATATTTCAAGTGCCTAGACTGTTACTTTGGCAATTTCCTGG
1588 CCCTCCACTCCTCATCCCACAATCTGGCTTAGTGCCACCCACCTTTGCCACAAAGCTAGGATGGTTCT
1657 GTGACCCATCTGTAGTAATTTATTGTCTGTCTACATTTCTGCAGATCTTCCGTGGTCAGAGTGCCACTG
1726 CGGGAGCTCTGTATGGTCAGGATGTAGGGGTTAACTTGGTCAGAGCCACTCTATGAGTTGGACTTCAGT
1795 CTTGCCTAGGCGATTTTGTCTACCATTTGTGTTTTGAAAGCCCAAGGTGCTGATGTCAAAGTGTAACAG
1864 ATATCAGTGTCTCCCCGTGTCCTCTCCCTGCCAAGTCTCAGAAGAGGTTGGGCTTCCATGCCTGTAGCT
1933 TTCCTGGTCCCTCACCCCATGGCCCCAGGCCACAGCGTGGGAACTCACTTTCCCTTGTGTCAAGACAT
2002 TTCTCTAACTCCTGCCATTCTTCTGGTGCTACTCCATGCAGGGGTCAGTGCAGCAGAGGACAGTCTGGA
2071 GAAGGTATTAGCAAAGCAAAAGGCTGAGAAGGAACAGGGAACATTGGAGCTGACTGTTCTTGGTAACTG
2140 ATTACCTGCCAATTGCTACCGAGAAGGTTGGAGGTGGGGAAGGCTTTGTATAATCCCACCCACCTCACC
2209 AAAACGATGAAGGTATGCTGTCATGGTCCTTTCTGGAAGTTTCTGGTGCCATTTCTGAACTGTTACAAC
2278 TTGTATTTCCAAACCTGGTTCATATTTATACTTTGCAATCCAAATAAAGATAACCCTTATTCCATAAAA
2347 AAAAAAAAAAAAAA
```

FIG. 3

```
ACTTTATCCTCCAAGCCACAAGCACTGGCCACAAACAAGGAGGACGGGAAAAGAAGAAGAAA    GACTTGCAAGAGGCAGATCTGGACCTTTGAGAGTC
 T  L  S  S  K  P  Q  A  L  A  T  P  N  K  E  E  H  G  K  R  K  K  K     D  L  Q  E  A  D  L  D  L  L  R  V
                        80                            90                                              70

GGCAAGGGGCTAGGGAAGAAGAGAAGAGGGACCCATGTCTTCGGAAATACAAGGACTTCTGCATCCATGGAGAA
 G  K  G  L  G  K  K  R  D  P  C  L  R  K  Y  K  D  F  C  I  H  G  E
                       100                           110                           120

TGCAAATATGTGAAGGAGCTCCGGGCTCCCTCTGCATCTGCCACCCGGGTTACCATGGAGAGAGGTGT
 C  K  Y  V  K  E  L  R  A  P  S  C  I  C  H  P  G  Y  H  G  E  R  C
                                      130                           140

CATGGGCTGAGCCTC
 H  G  L  S  L
```

FIG. 4

```
CAT ATG GAG AAA AAA ATC ACT GGA TAT ACC ACC GTT GAT ATA TCC CAA    48
    Met Glu Lys Lys Ile Thr Gly Tyr Thr Thr Val Asp Ile Ser Gln
    1                   5                  10                  15

TAT CAT CGT AAA GAA CAT TTT GAG GCA TTT CAG TCA GTT CAA GCT TCA    96
Tyr His Arg Lys Glu His Phe Glu Ala Phe Gln Ser Val Gln Ala Ser
                20                  25                  30

ACC TAT AAC CAG ACC GTT ACC GTT CAG CTG GAT ATT GCC TTT TTA AAG ACC   144
Thr Tyr Asn Gln Thr Val Thr Val Gln Leu Asp Ile Ala Phe Leu Lys Thr
        35                  40                  45

GTA AAG AAT AAG CAC AAG TTT TAT CCG GCC TTT ATT CAC ATT CTT   192
Val Lys Asn Lys His Lys Phe Tyr Pro Ala Phe Ile His Ile Leu
        50                  55                  60

GCC CGC CTG CTG AAT GCT CAT CCG GAA TTC ATG AGA GTC ACT TTA TCC   240
Ala Arg Leu Leu Asn Ala His Pro Glu Phe Met Arg Val Thr Leu Ser
    65                  70                  75

TCC AAG CCA CAA GCA CTG CTA GGG AAG CTA AAC CCA AAG AGG GAG GAG AAA   288
Ser Lys Pro Gln Ala Leu Ala Thr Pro Asn Lys Lys Arg Glu Glu Lys
80                  85                  90                  95

AGA AAG AAA GGC AAG AAA GGG CTA GGG AAG GAG AGG GAC CCA TGT CTT   336
Arg Lys Lys Gly Lys Lys Gly Leu Gly Lys Glu Arg Asp Pro Cys Leu
                100                 105                 110

CGG AAA TAC AAG GAC TTC TGC ATC CAT GGA GAA TGC AAA TAT GTG AAG   384
Arg Lys Tyr Lys Asp Phe Cys Ile His Gly Glu Cys Lys Tyr Val Lys
        115                 120                 125

GAG CTC CGG GCT CCC TCC TGC ATC TGC CAC CCG GGT TAC CAT GGA GAG   432
Glu Leu Arg Ala Pro Ser Cys Ile Cys His Pro Gly Tyr His Gly Glu
130                 135                 140

AGG TGT CAT GGG CTG AGC TAAGCTT   457
Arg Cys His Gly Leu Ser
145
```

FIG. 5

SEQUENCE LISTING ( 1 ) GENERAL INFORMATION:

( i i i ) NUMBER OF SEQUENCES: 18

( 2 ) INFORMATION FOR SEQ ID NO: 1:

( i ) SEQUENCE CHARACTERISTICS:
        ( A ) LENGTH: 2360 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GCTACGCGGG  CCACGCTGCT  GGCTGGCCTG  ACCTAGGCGC  GCGGGGTCGG  GCGGCCGCGC        60

GGGCGGGCTG  AGTGAGCAAG  ACAAGACACT  CAAGAAGAGC  GAGCTGCGCC  TGGGTCCCGG       120

CCAGGCTTGC  ACGCAGAGGC  GGGCGGCAGA  CGGTGCCCGG  CGGAATCTCC  TGAGCTCCGC       180

CGCCCAGCTC  TGGTGCCAGC  GCCCAGTGGC  CGCCGCTTCG  AAAGTGACTG  GTGCCTCGCC       240

GCCTCCTCTC  GGTGCGGGAC  C ATG AAG CTG CTG CCG TCG GTG GTG CTG AAG            291
             Met Lys Leu Leu Pro Ser Val Val Leu Lys
              1               5                  10

CTC TTT CTG GCT GCA GTT CTC TCG GCA CTG GTG ACT GGC GAG AGC CTG             339
Leu Phe Leu Ala Ala Val Leu Ser Ala Leu Val Thr Gly Glu Ser Leu
              15                  20                  25

GAG CGG CTT CGG AGA GGG CTA GCT GCT GGA ACC AGC AAC CCG GAC CCT             387
Glu Arg Leu Arg Arg Gly Leu Ala Ala Gly Thr Ser Asn Pro Asp Pro
         30                  35                  40

CCC ACT GTA TCC ACG GAC CAG CTG CTA CCC CTA GGA GGC GGC CGG GAC             435
Pro Thr Val Ser Thr Asp Gln Leu Leu Pro Leu Gly Gly Gly Arg Asp
             45                  50                  55

CGG AAA GTC CGT GAC TTG CAA GAG GCA GAT CTG GAC CTT TTG AGA GTC             483
Arg Lys Val Arg Asp Leu Gln Glu Ala Asp Leu Asp Leu Leu Arg Val
     60                  65                  70

ACT TTA TCC TCC AAG CCA CAA GCA CTG GCC ACA CCA AAC AAG GAG GAG             531
Thr Leu Ser Ser Lys Pro Gln Ala Leu Ala Thr Pro Asn Lys Glu Glu
 75                  80                  85                  90

CAC GGG AAA AGA AAG AAG AAA GGC AAG GGG CTA GGG AAG AAG AGG GAC             579
His Gly Lys Arg Lys Lys Lys Gly Lys Gly Leu Gly Lys Lys Arg Asp
                 95                 100                 105

CCA TGT CTT CGG AAA TAC AAG GAC TTC TGC ATC CAT GGA GAA TGC AAA             627
Pro Cys Leu Arg Lys Tyr Lys Asp Phe Cys Ile His Gly Glu Cys Lys
            110                 115                 120

TAT GTG AAG GAG CTC CGG GCT CCC TCC TGC ATC TGC CAC CCG GGT TAC             675
Tyr Val Lys Glu Leu Arg Ala Pro Ser Cys Ile Cys His Pro Gly Tyr
        125                 130                 135

CAT GGA GAG AGG TGT CAT GGG CTG AGC CTC CCA GTG GAA AAT CGC TTA             723
His Gly Glu Arg Cys His Gly Leu Ser Leu Pro Val Glu Asn Arg Leu
    140                 145                 150

TAT ACC TAT GAC CAC ACA ACC ATC CTG GCC GTG GTG GCT GTG GTG CTG             771
Tyr Thr Tyr Asp His Thr Thr Ile Leu Ala Val Val Ala Val Val Leu
155                 160                 165                 170
```

| | | | | | | | | | | | | | | | | |
|---|---|---|---|---|---|---|---|---|---|---|---|---|---|---|---|---|
| TCA | TCT | GTC | TGT | CTG | CTG | GTC | ATC | GTG | GGG | CTT | CTC | ATG | TTT | AGG | TAC | 819 |
| Ser | Ser | Val | Cys | Leu | Leu | Val | Ile | Val | Gly | Leu | Leu | Met | Phe | Arg | Tyr | |
| | | | | 175 | | | | | 180 | | | | | 185 | | |
| CAT | AGG | AGA | GGA | GGT | TAT | GAT | GTG | GAA | AAT | GAA | GAG | AAA | GTG | AAG | TTG | 867 |
| His | Arg | Arg | Gly | Gly | Tyr | Asp | Val | Glu | Asn | Glu | Glu | Lys | Val | Lys | Leu | |
| | | | 190 | | | | | 195 | | | | | 200 | | | |
| GGC | ATG | ACT | AAT | TCC | CAC | TGAGAGAGAC | | TTGTGCTCAA | | GGAATCGGCT | | | | | | 915 |
| Gly | Met | Thr | Asn | Ser | His | | | | | | | | | | | |
| | | 205 | | | | | | | | | | | | | | |

| | | | | |
|---|---|---|---|---|
| GGGGACTGCT | ACCTCTGAGA | AGACACAAGG | TGATTTCAGA | CTGCAGAGGG | GAAAGACTTC | 975 |
| CATCTAGTCA | CAAAGACTCC | TTCGTCCCCA | GTTGCCGTCT | AGGATTGGGC | CTCCCATAAT | 1035 |
| TGCTTTGCCA | AAATACCAGA | GCCTTCAAGT | GCCAAACAGA | GTATGTCCGA | TGGTATCTGG | 1095 |
| GTAAGAAGAA | AGCAAAAGCA | AGGGACCTTC | ATGCCCTTCT | GATTCCCCTC | CACCAAACCC | 1155 |
| CACTTCCCCT | CATAAGTTTG | TTTAAACACT | TATCTTCTGG | ATTAGAATGC | CGGTTAAATT | 1215 |
| CCATATGCTC | CAGGATCTTT | GACTGAAAAA | AAAAAAGAAG | AAGAAGAAGG | AGAGCAAGAA | 1275 |
| GGAAAGATTT | GTGAACTGGA | AGAAAGCAAC | AAAGATTGAG | AAGCCATGTA | CTCAAGTACC | 1335 |
| ACCAAGGGAT | CTGCCATTGG | GACCCTCCAG | TGCTGGATTT | GATGAGTTAA | CTGTGAAATA | 1395 |
| CCACAAGCCT | GAGAACTGAA | TTTTGGGACT | TCTACCCAGA | TGGAAAAATA | ACAACTATTT | 1455 |
| TTGTTGTTGT | TGTTTGTAAA | TGCCTCTTAA | ATTATATATT | TATTTTATTC | TATGTATGTT | 1515 |
| AATTTATTTA | GTTTTTAACA | ATCTAACAAT | AATATTTCAA | GTGCCTAGAC | TGTTACTTTG | 1575 |
| GCAATTTCCT | GGCCCTCCAC | TCCTCATCCC | CACAATCTGG | CTTAGTGCCA | CCCACCTTTG | 1635 |
| CCACAAAGCT | AGGATGGTTC | TGTGACCCAT | CTGTAGTAAT | TTATTGTCTG | TCTACATTTC | 1695 |
| TGCAGATCTT | CCGTGGTCAG | AGTGCCACTG | CGGGAGCTCT | GTATGGTCAG | GATGTAGGGG | 1755 |
| TTAACTGGT | CAGAGCCACT | CTATGAGTTG | GACTTCAGTC | TTGCCTAGGC | GATTTTGTCT | 1815 |
| ACCATTTGTG | TTTTGAAAGC | CCAAGGTGCT | GATGTCAAAG | TGTAACAGAT | ATCAGTGTCT | 1875 |
| CCCCGTGTCC | TCTCCCTGCC | AAGTCTCAGA | AGAGGTTGGG | CTTCCATGCC | TGTAGCTTTC | 1935 |
| CTGGTCCCTC | ACCCCATGG | CCCCAGGCCA | CAGCGTGGGA | ACTCACTTTC | CCTTGTGTCA | 1995 |
| AGACATTTCT | CTAACTCCTG | CCATTCTTCT | GGTGCTACTC | CATGCAGGGG | TCAGTGCAGC | 2055 |
| AGAGGACAGT | CTGGAGAAGG | TATTAGCAAA | GCAAAAGGCT | GAGAAGGAAC | AGGGAACATT | 2115 |
| GGAGCTGACT | GTTCTTGGTA | ACTGATTACC | TGCCAATTGC | TACCGAGAAG | GTTGGAGGTG | 2175 |
| GGGAAGGCTT | TGTATAATCC | CACCCACCTC | ACCAAAACGA | TGAAGGTATG | CTGTCATGGT | 2235 |
| CCTTTCTGGA | AGTTTCTGGT | GCCATTTCTG | AACTGTTACA | ACTTGTATTT | CCAAACCTGG | 2295 |
| TTCATATTTA | TACTTTGCAA | TCCAAATAAA | GATAACCCTT | ATTCCATAAA | AAAAAAAAA | 2355 |
| AAAAA | | | | | | 2360 |

( 2 ) INFORMATION FOR SEQ ID NO: 2:

( i ) SEQUENCE CHARACTERISTICS:
        ( A ) LENGTH: 208 amino acids
        ( B ) TYPE: amino acid
        ( C ) STRANDEDNESS: Not Relevant
        ( D ) TOPOLOGY: linear ( x i ) SEQUENCE DESCRIPTION: SEQ ID NO: 2:

| | | | | | | | | | | | | | | |
|---|---|---|---|---|---|---|---|---|---|---|---|---|---|---|
| Met | Lys | Leu | Leu | Pro | Ser | Val | Val | Leu | Lys | Leu | Phe | Leu | Ala | Ala | Val |
| 1 | | | | 5 | | | | | 10 | | | | | 15 | |
| Leu | Ser | Ala | Leu | Val | Thr | Gly | Glu | Ser | Leu | Glu | Arg | Leu | Arg | Arg | Gly |
| | | | | 20 | | | | | 25 | | | | | 30 | |

| | | | | | | | | | | | | | | |
|---|---|---|---|---|---|---|---|---|---|---|---|---|---|---|
| Leu | Ala | Ala | Gly | Thr | Ser | Asn | Pro | Asp | Pro | Pro | Thr | Val | Ser | Thr | Asp |
| | | 35 | | | | 40 | | | | | 45 | | | |
| Gln | Leu | Leu | Pro | Leu | Gly | Gly | Gly | Arg | Asp | Arg | Lys | Val | Arg | Asp | Leu |
| | 50 | | | | | 55 | | | | | 60 | | | | |
| Gln | Glu | Ala | Asp | Leu | Asp | Leu | Leu | Arg | Val | Thr | Leu | Ser | Ser | Lys | Pro |
| 65 | | | | | 70 | | | | | 75 | | | | | 80 |
| Gln | Ala | Leu | Ala | Thr | Pro | Asn | Lys | Glu | Glu | His | Gly | Lys | Arg | Lys | Lys |
| | | | | 85 | | | | | 90 | | | | | 95 | |
| Lys | Gly | Lys | Gly | Leu | Gly | Lys | Lys | Arg | Asp | Pro | Cys | Leu | Arg | Lys | Tyr |
| | | | 100 | | | | | 105 | | | | | 110 | | |
| Lys | Asp | Phe | Cys | Ile | His | Gly | Glu | Cys | Lys | Tyr | Val | Lys | Glu | Leu | Arg |
| | | 115 | | | | | 120 | | | | | 125 | | | |
| Ala | Pro | Ser | Cys | Ile | Cys | His | Pro | Gly | Tyr | His | Gly | Glu | Arg | Cys | His |
| | 130 | | | | | 135 | | | | | 140 | | | | |
| Gly | Leu | Ser | Leu | Pro | Val | Glu | Asn | Arg | Leu | Tyr | Thr | Tyr | Asp | His | Thr |
| 145 | | | | | 150 | | | | | 155 | | | | | 160 |
| Thr | Ile | Leu | Ala | Val | Val | Ala | Val | Val | Leu | Ser | Ser | Val | Cys | Leu | Leu |
| | | | | 165 | | | | | 170 | | | | | 175 | |
| Val | Ile | Val | Gly | Leu | Leu | Met | Phe | Arg | Tyr | His | Arg | Arg | Gly | Gly | Tyr |
| | | | 180 | | | | | 185 | | | | | 190 | | |
| Asp | Val | Glu | Asn | Glu | Glu | Lys | Val | Lys | Leu | Gly | Met | Thr | Asn | Ser | His |
| | | 195 | | | | | 200 | | | | | 205 | | | |

( 2 ) INFORMATION FOR SEQ ID NO: 3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO: 3:

| | | | | | | | | | | | | | | |
|---|---|---|---|---|---|---|---|---|---|---|---|---|---|---|
| Val | Xaa | Leu | Ser | Ser | Lys | Pro | Gln | Ala | Leu | Ala | Xaa | Pro | Asn | Lys | Glu |
| 1 | | | | 5 | | | | | 10 | | | | | 15 | |
| Glu | His | Gly | Lys | | | | | | | | | | | | |
| | | | 20 | | | | | | | | | | | | |

( 2 ) INFORMATION FOR SEQ ID NO: 4:

( i ) SEQUENCE CHARACTERISTICS:
        ( A ) LENGTH: 51 amino acids
        ( B ) TYPE: amino acid
        ( C ) STRANDEDNESS: single
        ( D ) TOPOLOGY: linear ( x i ) SEQUENCE DESCRIPTION: SEQ ID NO: 4:

| | | | | | | | | | | | | | | |
|---|---|---|---|---|---|---|---|---|---|---|---|---|---|---|
| Arg | Val | Xaa | Leu | Ser | Ser | Lys | Pro | Gln | Ala | Leu | Ala | Xaa | Pro | Asn | Lys |
| 1 | | | | 5 | | | | | 10 | | | | | 15 | |
| Glu | Glu | His | Gly | Lys | Arg | Lys | Lys | Lys | Gly | Lys | Gly | Leu | Gly | Lys | Lys |
| | | | 20 | | | | | 25 | | | | | 30 | | |
| Arg | Asp | Pro | Xaa | Leu | Arg | Lys | Tyr | Lys | Asp | Phe | Xaa | Ile | His | Gly | Glu |
| | | 35 | | | | | 40 | | | | | 45 | | | |
| Xaa | Xaa | Tyr | | | | | | | | | | | | | |
| | | 50 | | | | | | | | | | | | | |

( 2 ) INFORMATION FOR SEQ ID NO: 5:

( i ) SEQUENCE CHARACTERISTICS:
        ( A ) LENGTH: 18 amino acids
        ( B ) TYPE: amino acid
        ( C ) STRANDEDNESS: single ( D ) TOPOLOGY: linear ( x i ) SEQUENCE DESCRIPTION: SEQ ID NO: 5:

Arg Val Xaa Leu Ser Ser Lys Pro Gln Ala Leu Ala Xaa Pro Asn Lys
1               5                   10                  15

Glu Glu ( 2 ) INFORMATION FOR SEQ ID NO: 6:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( x i ) SEQUENCE DESCRIPTION: SEQ ID NO: 6:

Ser Ser Lys Pro Gln Ala Leu Ala Xaa Xaa Asn Xaa Glu Glu
1               5                   10

( 2 ) INFORMATION FOR SEQ ID NO: 7:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( x i ) SEQUENCE DESCRIPTION: SEQ ID NO: 7:

Ala Leu Ala Xaa Xaa Asn Lys Xaa Glu Xaa Gly Lys Arg
1               5                   10

( 2 ) INFORMATION FOR SEQ ID NO: 8:

( i ) SEQUENCE CHARACTERISTICS:
    ( A ) LENGTH: 24 amino acids
    ( B ) TYPE: amino acid
    ( C ) STRANDEDNESS: single
    ( D ) TOPOLOGY: linear ( x i ) SEQUENCE DESCRIPTION: SEQ ID NO: 8:

Arg Val Xaa Leu Ser Ser Lys Pro Gln Ala Leu Ala Xaa Pro Asn Lys
1               5                   10                  15

Glu Glu His Gly Lys Arg Lys Lys
                20

( 2 ) INFORMATION FOR SEQ ID NO: 9:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( x i ) SEQUENCE DESCRIPTION: SEQ ID NO: 9:

Xaa Xaa Lys Pro Gln Ala Leu Ala Xaa Xaa Asn Xaa Glu
1               5                   10

( 2 ) INFORMATION FOR SEQ ID NO: 10:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( x i ) SEQUENCE DESCRIPTION: SEQ ID NO: 10:

Ala Leu Ala Xaa Pro Asn Lys Glu Glu Xaa Gly Lys Arg ( 2 ) INFORMATION FOR SEQ ID NO: 11:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 4
        ( D ) OTHER INFORMATION: /note= "Nucleotide number 4 may be T."

( i x ) FEATURE:
        ( A ) NAME/KEY: misc_feature
        ( B ) LOCATION: 22
        ( D ) OTHER INFORMATION: /note= "Nucleotide number 22 may be G"

( i x ) FEATURE:
        ( A ) NAME/KEY: misc_feature
        ( B ) LOCATION: 40
        ( D ) OTHER INFORMATION: /note= "Nucleotide number 40 may be G."

( x i ) SEQUENCE DESCRIPTION: SEQ ID NO: 11:

CTTGCCATGC TCCTCCTTGT TAGGCTTGGC CAGGGCCTGA GGCTT    45

( 2 ) INFORMATION FOR SEQ ID NO: 12:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 7
        ( D ) OTHER INFORMATION: /note= "Nucleotide number 7 may be G"

( x i ) SEQUENCE DESCRIPTION: SEQ ID NO: 12:

GCCGCCACCA TGG    13

( 2 ) INFORMATION FOR SEQ ID NO: 13:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( x i ) SEQUENCE DESCRIPTION: SEQ ID NO: 13:

Cys Asn Ala Glu Phe Gln Asn Phe Cys Ile His Gly Glu Cys Lys Tyr
1                5                          10                      15

Ile Glu His Leu Glu Ala Val Thr Cys Lys Cys Gln Gln Glu Tyr Phe
                20                    25                        30

Gly Glu Arg Cys
          35

( 2 ) INFORMATION FOR SEQ ID NO: 14:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( x i ) SEQUENCE DESCRIPTION: SEQ ID NO: 14:

Cys Pro Leu Ser His Asp Gly Tyr Cys Leu His Asp Gly Val Cys Met

```
              1               5                    10                        15
           Tyr Ile Glu Ala Leu Asp Lys Tyr Ala Cys Asn Cys Val Val Gly Tyr
                           20                  25                  30
           Ile Gly Glu Arg Cys
                   35
```

( 2 ) INFORMATION FOR SEQ ID NO: 15:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( x i ) SEQUENCE DESCRIPTION: SEQ ID NO: 15:

```
           Cys Pro Asp Ser His Thr Gln Phe Cys Phe His Gly Thr Cys Arg Phe
           1               5                   10                       15
           Leu Val Gln Glu Asp Lys Pro Ala Cys Val Cys His Ser Gly Tyr Val
                           20                  25                  30
           Gly Ala Arg Cys
                   35
```

( 2 ) INFORMATION FOR SEQ ID NO: 16:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO: 16:

```
           Asp Leu Gln Glu Ala Asp Leu Asp Leu Leu Arg Val Xaa Leu Xaa Ser
           1               5                   10                       15
```

( 2 ) INFORMATION FOR SEQ ID NO: 17:

( i ) SEQUENCE CHARACTERISTICS:
        ( A ) LENGTH: 457 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

```
CATATGGAGA   AAAAAATCAC   TGGATATACC   ACCGTTGATA   TATCCCAATA   TCATCGTAAA       60
GAACATTTTG   AGGCATTTCA   GTCAGTTGCT   CAATCAACCT   ATAACCAGAC   CGTTCAGCTG      120
GATATTACGG   CCTTTTTAAA   GACCGTAAAG   AAAAATAAGC   ACAAGTTTTA   TCCGGCCTTT      180
ATTCACATTC   TTGCCCGCCT   GCTGAATGCT   CATCCGGAAT   TCATGAGAGT   CACTTTATCC      240
TCCAAGCCAC   AAGCACTGGC   CACACCAAAC   AAGGAGGAGC   ACGGGAAAAG   AAAGAAGAAA      300
GGCAAGGGGC   TAGGGAAGAA   GAGGGACCCA   TGTCTTCGGA   AATACAAGGA   CTTCTGCATC      360
CATGGAGAAT   GCAAATATGT   GAAGGAGCTC   CGGGCTCCCT   CCTGCATCTG   CCACCCGGGT      420
TACCATGGAG   AGAGGTGTCA   TGGGCTGAGC   TAAGCTT                                   457
```

( 2 ) INFORMATION FOR SEQ ID NO: 18:

( i ) SEQUENCE CHARACTERISTICS:
        ( A ) LENGTH: 149 amino acids
        ( B ) TYPE: amino acid
        ( C ) STRANDEDNESS: single
        ( D ) TOPOLOGY: linear ( x i ) SEQUENCE DESCRIPTION: SEQ ID NO: 18:

-continued

```
Met  Glu  Lys  Lys  Ile  Thr  Gly  Tyr  Thr  Thr  Val  Asp  Ile  Ser  Gln  Tyr
                    5                        10                       15

His  Arg  Lys  Glu  His  Phe  Glu  Ala  Phe  Gln  Ser  Val  Ala  Gln  Ser  Thr
               20                       25                       30

Tyr  Asn  Gln  Thr  Val  Gln  Leu  Asp  Ile  Thr  Ala  Phe  Leu  Lys  Thr  Val
          35                       40                       45

Lys  Lys  Asn  Lys  His  Lys  Phe  Tyr  Pro  Ala  Phe  Ile  His  Ile  Leu  Ala
     50                       55                       60

Arg  Leu  Leu  Asn  Ala  His  Pro  Glu  Phe  Met  Arg  Val  Thr  Leu  Ser  Ser
65                       70                       75                       80

Lys  Pro  Gln  Ala  Leu  Ala  Thr  Pro  Asn  Lys  Glu  Glu  His  Gly  Lys  Arg
                    85                       90                       95

Lys  Lys  Lys  Gly  Lys  Gly  Leu  Gly  Lys  Lys  Arg  Asp  Pro  Cys  Leu  Arg
               100                      105                      110

Lys  Tyr  Lys  Asp  Phe  Cys  Ile  His  Gly  Glu  Cys  Lys  Tyr  Val  Lys  Glu
          115                      120                      125

Leu  Arg  Ala  Pro  Ser  Cys  Ile  Cys  His  Pro  Gly  Tyr  His  Gly  Glu  Arg
     130                      135                      140

Cys  His  Gly  Leu  Ser
145
```

HEPARIN BINDING MITOGEN WITH HOMOLOGY TO EPIDERMAL GROWTH FACTOR (EGF)

This application is a continuation-in-part of Klagsbrun et al., U.S. Ser. No. 07/598,082, filed Oct. 16, 1990 now abandoned.

This invention was made with Government support under #R37CA37392 awarded by the National Institute of Health. The government has certain rights in the invention.

BACKGROUND OF THE INVENTION

This invention relates to growth factors.

Growth factors play a central role in mediating cell proliferation and differentiation, for example, basic fibroblast growth factor (bFGF), platelet-derived growth factor (PDGF), transforming growth factor-alpha (TGF-α), and transforming growth factor-beta (TGF-β) have been implicated in the proliferation of connective tissue cells and the induction of angiogenesis characteristic of wound repair (Van Brunt and Klausner, 6 *Biotechnology* 25, 1988). In addition, Agel et al. (146 *J. Pathol.* 197, 1985) suggest that growth factors are involved in the etiology of atherosclerosis; for example, the smooth muscle cell (SMC) hyperplasia that accompanies atherosclerosis has been attributed to PDGF, a potent SMC mitogen.

Heparin affinity chromatography has been used extensively for purifying and characterizing a variety of these growth factors. Acidic FGF (aFGF) and basic FGF (bFGF) bind to immobilized heparin columns and are eluted with 1.0M to 1.2M NaCl and 1.5M to 1.8M NaCl, respectively (Folkman and Klagsbrun, 235 *Science* 442, 1987; Lobb et al., 261 *J. Biol. Chem.* 1924, 1986). Several growth factors which are structurally homologous to aFGF and bFGF also have an affinity for heparin (see, for example, Rubin et al., 86 *Proc. Natl. Acad. Sci. USA* 802, 1989). PDGF binds to immobilized heparin, but with relatively low affinity, being eluted with only 0.5M NaCl. Epidermal growth factor (EGF) does not bind heparin to any substantial extent under the conditions described in the cited references on heparin binding growth factors. Lobb et al. (261 *J. Biol. Chem.* 1924, 1986) report the partial purification by heparin affinity of two classes of growth factors mitogenic for endothelial cells. Gospodarowicz et al. (81 *Proc. Natl. Acad. Sci. USA* 6963, 1984) report the use of heparin affinity in the purification of bovine brain and pituitary fibroblast growth factors. Shing et al. (29 *J. Cell Biochem.* 275, 1985) report a chondrosarcoma-derived growth factor purified by heparin-Sepharose affinity chromatography and Bio Rex 70 cation exchange chromatography. Bohlen et al. (185 *FEBS Lett.* 177, 1985) report a fibroblast growth factor, derived from human brain, which is purified by cation-exchange chromatography, heparin-Sepharose affinity, and reverse-phase HPLC. Shing et al. (223 *Science* 1296, 1984) report a heparin-binding tumor cell-derived capillary endothelial cell factor. Besner et al. (107 *J. Cell Biol.* 481a, 1988) report the detection of a heparin-binding, mononuclear cell-derived growth factor(s) which is cationic, is of 6000–14,000 MW, is inactivated by heat (100° C., 10 min), is inactivated by dithiothreitol (5 mM), and is resistant to incubation with 4M guanidine or 0.1M HCl.

SUMMARY OF THE INVENTION

In one aspect, the invention generally features a novel growth factor which we have termed heparin binding EGF-homologous mitogen (HB-EHM). By "EGF homologous" is meant having a segment structurally related to epidermal growth factor in that it contains six cysteine residues spaced in a manner characteristic of any of the EGF family of proteins (e.g., human amphiregulin (AR), Shoyab et al., 243 *Science* 1074, 1989; human TGF-α, Derynck et al., 38 *Cell* 287, 1984; and human EGF, Gregory, 257 *Nature* 325, 1975), which participates in binding as described below to one or more of the EGF family of receptors (e.g., on A-431 cells or smooth muscle cells). In general, an EGF-homologous segment renders the protein including such a domain at least partially resistant to heat (e.g., following exposure to a temperature of 90° for 5 minutes) and sensitive to dithiothreitol (DTT) (e.g., following exposure to 5 mM DTT for 2 hours). "Heparin binding" means having a specific affinity for heparin (i.e., an affinity beyond that predicted only by ionic interactions) as evidenced by binding to heparin at NaCl concentrations above those which elute similarly charged proteins having no specific affinity. In general, heparin binding factors remain bound to heparin up to NaCl concentrations of at least 0.6M (most preferably, at least 0.9M).

In a second aspect, the invention features polypeptides which bind heparin, which include an EGF-homologous segment, and which stimulate growth of fibroblast cells, epithelial cells, and smooth muscle cells, but not endothelial cells.

In preferred embodiments, these polypeptides are human HB-EHM, and, more preferably, they include a characteristic EGF-homologous segment sequence (substantially, amino acids 108 to 143 of SEQ ID NO:2: C L R K Y K D F C I H G E C K Y V K E L R A P S C I C H P G Y H G E R C). One particular such peptide includes the above described EGF-homologous segment and all or part of amino acids 1 to 208 of SEQ ID NO:2: M K L L P S V V L K L F L A A V L S A L V T G E S L E R L R R G L A A G T S N P D P P T V S T D Q L L P L G G G R D R K V R D L Q E A D L D L L R V T L S S K P Q A L A T P N K E E H G K R K K K G K G L G K K R D P C L R K Y K D F C I H G E C K Y V K E L R A P S C I C H P G Y H G E R C H G L S L P V E N R L Y T Y D H T T I L A V V A V V L S S V C L L V I V G L L M F R Y H R R G G Y D V E N E E K V K L G M T N S H. In a mature form, HB-EHMs may have an amino-terminus between aspartic acid residue 63 and alanine residue 82 (as shown in FIG. 3, SEQ ID NO:2) and a carboxy-terminus between serine residue 147 and proline residue 149 (also as shown in FIG. 3, SEQ ID NO:2). The invention also encompasses smaller polypeptides, for example, those having an amino-terminus between arginine residue 73 and alanine residue 82 (as shown in FIG. 3, SEQ ID NO: 1) and is a carboxy-terminus at serine residue 147 (also as shown in FIG. 3, SEQ ID NO: 2). These polypeptides are preferably acid stable. The isolated polypeptide may contain a sequence substantially identical to the amino acid sequence shown in FIG. 1 (amino acids 82 to 147 in SEQ ID NO:2) or may contain a sequence substantially identical to the amino acid sequence shown in FIG. 4 (amino acids 63 to 148 in SEQ ID NO: 2). The polypeptides according to the invention are preferably cationic, may have a pI of between 7.2 and 7.8 (e.g., when produced by a eukaryotic cell), and may be, but need not be, glycosylated. Preferred polypeptides according to the invention have an apparent molecular weight of approximately 22,000 on a non-reducing polyacrylamide gel and include at least 66 amino acid residues. In addition, these polypeptides, preferably, are sufficiently isolated from other co-purifying substances to be suitable for therapeutic use.

In other aspects, the invention features: purified nucleic acid which encodes the polypeptides described above; vectors (preferably, pMTN-HBEGF, pAX-HBEGF, pNA28, and pNA51) which direct expression of this nucleic acid in eukaryotic (preferably, mammalian) or prokaryotic (preferably, *Escherichia coli*, most preferably, *E. coli* B or *E. coli* W3110) cells. The invention also features cells containing such vectors; such cells may be eukaryotic cells (for example, mammalian cells capable of secreting a mature form of the protein into the growth medium) or prokaryotic cells which are capable of producing a polypeptide which includes the primary sequence of a mature form of the protein and which may also include additional amino acids at the amino or carboxy terminus which facilitate improved expression, stability, or ease of isolation of the HB-EHM. The expression vectors or vector-containing cells of the invention can be used in a method of the invention to produce HB-EHM and equivalent polypeptides. These polypeptides can be used in a method of the invention for healing a wound in a patient, involving applying to the wound a wound healing amount of the polypeptides described above. The polypeptides can also be used in a method of the invention for the in vitro culturing of a cell whose proliferation is stimulated by HB-EHM, preferably, fibroblasts, epithelial cells, or smooth muscle cells, involving contacting the cells with a growth-stimulatory amount of the polypeptides described above. The polypeptides can further be used to produce an antibody which preferentially binds to the polypeptides. The antibody is preferably monoclonal and neutralizes the in vivo biological activity of the polypeptides described above.

In a final aspect, the invention features a method for identifying an antagonist to HB-EHM, involving providing HB-EHM to cultured cells whose growth is stimulated by this factor, in the presence of a candidate antagonist, and determining whether the candidate antagonist is capable of blocking HB-EHM-induced growth of the cells.

By "mature" is meant the protein in one of its processed extracellular forms. By "biological activity" is meant the ability of the factor to stimulate the growth of cells (e.g., fibroblasts, epithelial cells, or smooth muscle cells, but not endothelial cells) assayed, e.g., using the methods described below. By "isolated" is meant removed from its naturally-occurring environment and preferably produced as a homogeneous solution by standard biochemical or recombinant DNA techniques. By "acid stable" is meant retaining biological activity (as described above) following, e.g., exposure to a solution at pH 2.5 for 2 hours. By "glycosylated" is meant having one or more covalently-linked carbohydrate moieties. By "un-glycosylated" is meant lacking covalently-linked carbohydrate moieties. By "apparent molecular weight" is meant the molecular weight, determined on a denaturing polyacrylamide gel, by comparison with standards, e.g., protein standards, of known molecular weight. By "non-reducing polyacrylamide gel" is meant a polyacrylamide electrophoretic gel lacking a reducing agent such as β-mercaptoethanol. By "healing a wound" is meant, without limitation, stimulating tissue repair or blood vessel development. By an "antagonist" is meant a molecule which inhibits an activity of a factor, in this case, HB-EHM, such as the ability to stimulate the growth of responsive cells (e.g., fibroblasts, epithelial cells, and smooth muscle cells). By a "substantially identical" amino acid sequence is meant an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy the biological activity of the growth factor (as described above). Such equivalent growth factors can be isolated by extraction from the tissues or cells of any animal which naturally produce such a factor or which can be induced to do so, using the methods described below, or their equivalent; or can be isolated by chemical synthesis; or can be isolated by standard techniques of recombinant DNA technology, e.g., by isolation of cDNA or genomic DNA encoding such a growth factor. By a "substantially identical" nucleic acid sequence is meant a nucleic acid sequence which encodes a substantially identical amino acid sequence (i.e., one which is identical or which differs only by conservative amino acid substitutions, non-conservative amino acid substitutions, or deletions or insertions of amino acid sequence which do not destroy the biological activity of the factor, as described above). Such nucleic acid sequences may be isolated, without limitation, by standard techniques of recombinant DNA technology (e.g., by isolation of cDNA or genomic DNA, or by in vitro mutagenesis, by polymerase chain reaction methodology or by chemical synthesis). By "neutralize" is meant to partially or completely block (e.g., the biological activity of the growth factor).

This invention includes the growth factors, as translated (e.g., the 66 amino acid form of HB-EHM which include the amino acids shown in FIG. 1, or the 86 amino acid form of the HB-EHM shown in FIG. 4, or the 208 amino acid form of the protein shown in FIG. 3) as well as any growth-promoting forms of the protein which have undergone post-translational modification or processing. Such post-translational modification may include, without limitation, a processed amino-terminus, for example, removal of all or part of a signal sequence or all or part of a pro sequence; a processed carboxy-terminus, for example, removal of all or part of a membrane-spanning domain or all or part of a cytoplasmic domain; O-linked glycosylation; or any combination, thereof. Moreover, this invention is not limited to the amino acid or nucleic acid sequences provided in FIGS. 1, 3, or 4; those of ordinary skill in the art can readily isolate equivalent or substantially identical growth factors or nucleic acid sequences encoding equivalent or substantially identical growth factors using the methods described herein.

The growth factors of this invention play a role in the proliferative responses characteristic of wound repair, growth and development, atherosclerosis, neoplasia and myelofibrosis, and are therefore useful for stimulating the growth of cultured vertebrate cells, for enhancing the healing of wounds, and for detecting and treating atherosclerosis and neoplastic diseases.

Other features and advantages of the invention will be apparent from the following description of the preferred embodiments thereof, and from the claims.

The drawings will first briefly be described.

DRAWINGS

FIG. 1 is a representation of an amino acid sequence which is present in one form of mature (i.e., processed extracellular) heparin binding EGF-homologous mitogen.

FIG. 2 is a representation of the amino acid sequences of some EGF-homologous segments.

FIG. 3 is a representation of the nucleic acid sequence of a HB-EHM-encoding cDNA and the deduced amino acid sequence of the primary translation product.

FIG. 4 is a representation of an amino acid sequence which is present in at least one form of mature (i.e., processed extracellular) heparin binding EGF-homologous mitogen.

FIG. 5 is the nucleic acid and deduced amino acid sequence of the fusion protein chloramphenicol acetyltransferase (CAT)-HB-EHM.

BRIEF DESCRIPTION OF THE PREFERRED EMBODIMENTS

Derivation of Deposited Materials

Materials have been deposited with the American Type Culture Collection (ATCC) in Rockville, Md., which allow others skilled in the art to readily obtain the materials of this invention. The derivation of these deposited materials is described below. The growth factor produced by these deposited materials is exemplary of, not limiting to, this invention; those of ordinary skill in the art can readily isolate equivalent growth factors, nucleic acid encoding such growth factors, and antibodies which preferentially bind to such growth factors using the methods described below.

Isolation of Lymphoma Factor and Amino Acid Sequence

One source of heparin binding EGF-homologous mitogen (HB-EHM) is the human histiocytic lymphoma cell line U-937, available from the American Type Culture Collection, 12301 Parklawn Drive, Rockville, Md. 20852 (Accession No. CRL 1593). HB-EHM was isolated from this cell line as follows. U-937 cells were plated at 1–2 ×10$^8$ cells/T-150 flask (Costar, Cambridge, Mass.) in RPMI 1640 (GIBCO, Grand Island, N.Y.) supplemented with 10% fetal calf serum (GIBCO, Grand Island, N.Y.) and antibiotics (100 units/ml penicillin and 100 μg/ml streptomycin sulfate, GIBCO, Grand Island, N.Y.). Cells may be treated with 60 nM phorbol myristate acetate (PMA; also known as 12-O-tetradecanoyl phorbol-13-acetate; or TPA) for 24 hours at 37° to facilitate attachment of the cells to the tissue culture flask; however, this step is not necessary for HB-EHM production. Cells were washed twice with phosphate-buffered saline, and the medium was replaced with serum-free RPMI 1640 supplemented with antibiotics. After 72 hours at 37°, culture fluids were collected and replaced with the same amount of fresh serum-free medium, and the cells were again incubated for 72 hours until the next medium change. Cells were maintained in this way for 10–14 days, with continuous secretion of growth factors. Conditioned medium (CM) was collected every 3 days. The collected medium was centrifuged for 10 minutes at 10,000 rpm in a GS-3 Sorvall rotor, and benzamidine hydrochloride (Sigma, St. Louis, Mo.) was added to the supernatant to a final concentration of 1 mM to protect against protease degradation. The supernatant was stored at −20° C. until use.

Alternatively, conditioned medium was prepared by washing the PMA-treated cells with phosphate-buffered saline and replacing the medium with serum-free RPMI 1640 medium (as described above). The conditioned medium was then collected and replaced with fresh serum-free medium approximately 24, 48, 72, 120, and 168 hours later (i.e., after PMA treatment).

Conditioned medium was assayed for growth factor activity directly, as described below, using either fibroblasts (i.e., BALB/c mouse 3T3 cells), epithelial cells (i.e., human keratinocytes), or smooth muscle cells (i.e., bovine aortic smooth muscle cells, BASMC). Alternatively, CM was first fractionated by fast protein liquid chromatography (FPLC, Pharmacia, Piscataway, N.J.) by applying 500 ml of the CM to a TSK-heparin 5PW column (8×75 mm, TOSOHAAS, Philadelphia, Pa.). The column was washed with 10 column volumes of equilibration buffer (0.2M NaCl, 0.01M Tris-HCl, pH 7.5), and bound protein was eluted with a 40 ml linear gradient of 0.2–2M NaCl in 0.01M Tris-HCl , pH 7.4 at 1 ml/min. Fractions (2.5 ml) were tested for growth factor activity by measuring the effect of aliquots of the fractions on DNA synthesis in, or the proliferation of, BALB/c mouse 3T3 cells; such activity was monitored by assaying the incorporation of [$^3$H]-thymidine into DNA and/or by measuring the increase in cell number. Measurement of DNA synthesis in BALB/c mouse 3T3 cells was performed as described by Shing et al. (223 Science 1296, 1984, hereby incorporated by reference). One unit of BALB/c mouse 3T3 stimulation activity was defined as the amount of growth factor required to stimulate half-maximal DNA synthesis in BALB/c mouse 3T3 cells under the conditions described in Shing et al. (supra). To measure DNA synthesis in bovine capillary endothelial cells, cells were trypsinized and re-plated sparsely (1×10$^4$ cells/well) with 400 μl of Dulbecco's modified Eagle's medium (DMEM, GIBCO, Grand Island, N.Y.) supplemented with 10% bovine calf serum (GIBCO, Grand Island, N.Y.) and antibiotics (100 units/ml penicillin and 100 μg/ml streptomycin sulfate, GIBCO, Grand Island, N.Y.) in 48-well plates (Costar, Cambridge, Mass.). After 24 hours of incubation, the medium was replaced with the same volume of DMEM supplemented with 2% bovine calf serum, antibiotics, 1 μM thymidine and 0.5% bovine serum albumin. After 24 hours of incubation, the test samples were added to the wells. Eighteen hours later, [$^3$H]-thymidine (0.6 uCi/well, New England Nuclear, Wilmington, Del.) was added. After an additional 5 hours, each plate was treated by the same procedure as used to harvest the BALB/c mouse 3T3 cells to measure the incorporation of [$^3$H]-thymidine into the DNA of the cells. To measure DNA synthesis in bovine aortic smooth muscle cells (from Dr. H. Weich, Children's Hospital, Boston), the cells were trypsinized and re-plated sparsely (1×10$^4$ cells/well) with 400 μl of DMEM supplemented with 10% Colorado calf serum (Colorado Serum Company) and antibiotics (100 units/ml penicillin and 100 μg/ml streptomycin sulfate, GIBCO, Grand Island, N.Y.) in 48-well plates. After the cells were grown to confluence, the medium was replaced with the same volume of DMEM supplemented with 2% Colorado calf serum and antibiotics (as described above). After 24 hours of incubation, the test samples were added to the wells. Eighteen hours later, [$^3$H]-thymidine (1 uCi/well) was added. After an additional 6 hours, the plates were treated by the same procedure used to harvest the BALB/c mouse 3T3 and capillary endothelial cells to measure the incorporation of [$^3$H]-thymidine into the DNA of the cells.

Bovine aortic smooth muscle cell proliferation was also assayed by counting cell number following growth factor stimulation. In these experiments, cells were plated sparsely in 24 well plates in DMEM/10% bovine calf serum/1% GPS (100% GPS is glutamine 29.2 mg/ml, penicillin 10,000 units/ml, streptomycin sulfate 10,000 μg/ml; GIBCO, Grand Island, N.Y.) at 10$^4$ cells/well. Test samples were then added and, after three days, cells were removed by trypsinization and counted in a Coulter counter (Coulter, Hialeah, Fla.).

HB-EHM was purified as follows. Growth factor activity was monitored during the purification procedures using BALB/c mouse 3T3 cells as target cells and measuring [$^3$H]-thymidine incorporation into DNA. Conditioned medium (8-10L) was applied directly to a Bio-Rex 70 cation exchange column (5×10 cm, 200 ml) (BioRad, Hercules, Calif.) equilibrated with 0.2M NaCl, 0.01M Tris-HCl, pH 7.5, at a flow rate of 300 ml/hour. The column was washed extensively with the equilibration buffer, and the bound protein was eluted with 1M NaCl, 0.01M Tris-HCl, pH 7.5. The biologically active fractions (as assayed above using BALB/c mouse 3T3 cells) were adjusted to pH 8.0 and applied to a copper-chelating Sepharose column (2×11 cm, Pharmacia LKB Biotechnology Inc., Piscataway, N.J.) saturated with cupric sulfate and equilibrated with 0.5M NaCl, 0.01M Tris-HCl, pH 8.0. After washing extensively with the equilibration buffer, bound proteins were eluted with a 200 ml linear gradient of 0–0.04M L-histidine in 0.5M NaCl, 0.01M Tris-HCl, pH 8.0, at a flow rate of 40 ml/hour. Using this method, a single bioactive peak was eluted by 0.02M to 0.025M L-histidine. The biologically active fractions included in this peak of activity were pooled, diluted 1:1 with 0.01M Tris-HCl, pH 7.5, and applied to a TSK-heparin 5PW FPLC column (8×75 mm, TOSOHAAS, Philadelphia, Pa.) equilibrated with 0.2M NaCl, 0.01M Tris-HCl, pH 7.5. The column was washed with 20 ml of 0.2M NaCl, 0.01M Tris-HCl, pH 7.5, and bound protein was eluted with a 40 ml linear gradient of 0.2–2M NaCl in 0.01M Tris-HCl, pH 7.5, at a flow rate of 1 ml/min.

A partially purified HB-EHM sample prepared by the three step purification outlined above (and eluting from the TSK-heparin column at 1–1.2M NaCl) was applied to a $C_4$-reversed phase high performance liquid chromatography column (RP-HPLC). A Beckman model 334 HPLC system was used (Beckman Instruments, Inc., Somerset, N.J.). The sample was loaded onto the $C_4$-reversed phase HPLC column (4.6×250 mm, Vydac) after equilibration of the column with 5% acetonitrile, 0.1% trifluoroacetic acid. The column was washed with this solvent extensively, and bound proteins were eluted with a 5 ml gradient of 5%–15% acetonitrile, 0.1% trifluoroacetic acid followed by a 120 ml gradient of 15%–40% acetonitrile, 0.1% trifluoroacetic acid at a flow rate of 1 ml/min. Fractions were collected, and aliquots diluted 1 to 10 in 1% bovine serum albumin (Sigma, St. Louis, Mo.) in phosphate-buffered saline and analyzed for growth factor activity. Eluting protein was detected by monitoring absorbance at 214 nm.

A single predominant peak of growth factor activity was eluted from the $C_4$ column with approximately 23% acetonitrile. This peak of activity corresponded to two peaks of growth factor absorbance at 214 nM (i.e., a peak which eluted at 33 minutes and a peak which eluted at 34.5 minutes). Fractions were collected that corresponded to the first of these two peaks (i.e., the 33 minute peak) and were further analyzed. The purified protein migrated as a single band with an apparent molecular weight of about 22 kD under non-reducing conditions (i.e., on a 15% polyacrylamide/SDS gel) and an apparent molecular weight of 20 kD under reducing conditions (i.e., on a 15% polyacrylamide/SDS gel containing 1% β-mercaptoethanol). The apparent molecular weight of the growth factor was determined by comparing the electrophoretic migration of the factor with the electrophoretic migration of proteins of known molecular weight.

As measured by the factor's growth-stimulatory activity (assayed as [$^3$H]-thymidine incorporation into Balb/c mouse 3T3 cellular DNA by methods described above), this purified form of HB-EHM was resistant to exposure to pH 2.5 for 2 hours and not destroyed by heating to 90° C. for 5 minutes but was destroyed completely by exposure to 5 mM DTT for 2 hours. The activity was also not lost after acid treatment with 0.1M glycine-HCl, pH 2.5 for 2 hours.

In all of these procedures, tubes siliconized by Sigmacote (Sigma) were used to avoid loss of activity resulting from protein adsorption to the glass tubes.

The purification of one representive 8 L preparation of conditioned medium is summarized in the following table.

PURIFICATION OF HB-EHM FROM U-937 CONDITIONED MEDIUM

| Purification step | Protein (ug) | Maximal[a] Stimulation (ng/ml) | Purification (fold) | Yield[c] (%) |
|---|---|---|---|---|
| Bio-Rex 70 | 450,000[b] | 3,750 | 1 | 100% |
| Cu-chelating Sepharose | 90,000[b] | 3,700 | 1 | 23% |
| TSK-Heparin | 295[d] | 16.4 | 229 | 18% |
| $C_4$ RP-HPLC | 1.2[e] | 0.5 | 7,500 | 15% |

[a]The maximal stimulation was determined from $^3$[H]-thymidine incorporation into smooth muscle cell DNA.
[b]Protein was estimated by using $A_{280}^{1\%} = 14$ μg.
[c]The yield was based on the total activity in the first partially purified fraction.
[d]Protein was estimated by using $A_{214}^{1\%} = 140$ μg.
[e]Protein was estimated by amino acid analysis.

This purified form of the protein stimulated proliferation of BALB/c mouse 3T3 fibroblast cells at a concentration between 50 pg/ml and 1,000 pg/ml; stimulated proliferation of bovine aortic smooth muscle cells at a concentration between 50 pg/ml and 500 pg/ml, and stimulated proliferation of human keratinocytes at a concentration between 100 pg/ml and 2 ng/ml. The factor, however, did not stimulate proliferation of bovine capillary endothelial cells.

To determine the amino acid sequence of this purified form of the protein, approximately 1.7 μg of protein obtained after cation exchange, copper-affinity, and heparin-affinity chromatography and two cycles of $C_4$-reversed phase HPLC of 20 L of conditioned medium were loaded onto an Applied Biosystems gas-phase protein sequencer. Twenty rounds of Edman degradation were carried out, and identifications of amino acid derivatives were made with an automated on-line PTH-amino acid analyzer (model 477A, Applied Biosystems, Foster City, Calif.). The yield of the amino-terminal residue was 177 pmoles. Amino acid assignments made for cycles 1–20 were as follows (SEQ ID NO: 3): Val-X-Leu-Ser-Ser-Lys-Pro-Gln-Ala-Leu-Ala-X-Pro-Asn-Lys-Glu-Glu-His-Gly-Lys, where X is unknown or questionable.

In subsequent purification of HB-EHM from U-937 conditioned medium (as described above), a different $C_4$ column was used for the RP-HPLC purification steps, and BALB/c 3T3 $^3$[H]-thymidine incorporation assays were carried out using ten-fold higher amounts of protein from each fraction. Using such methods, four major peaks of growth factor activity were eluted from the column at 33, 34.5, 43.3, and 47.8 minutes subsequent to the start of a 15%–40% acetonitrile gradient. On a non-reducing 15% polyacrylamide/SDS gel, the 33, 43.3, and 47.8 minute peaks of activity corresponded to proteins of apparent molecular weight: 22, 23, and 22.5 kD, respectively. The 34.5 minute peak sometimes displayed two protein bands, one of apparent molecular weight 22 kD and the other of apparent molecular weight 19 kD; in other preparations, only the band of apparent molecular weight 19 kD band was detected. A fifth peak of growth factor activity was also detected in some preparations. This peak eluted between the 34.5 and the 43.3 minute peaks and contained a protein species of apparent molecular weight 24 kD under non-reducing polyacrylamide/SDS gel electrophoresis conditions.

The most predominant form of HB-EHM in these purifications was generally the form eluting at 33 minutes.

The specific activities of the additional growth factor species were analyzed; all were found to be nearly equivalent in their ability to stimulate DNA synthesis in BALB/c 3T3 cells and to compete with $^{125}$I-EGF (see below) for binding to the EGF receptor. These results suggested that the growth factor species contained in the different isolated peaks all corresponded to forms of HB-EHM.

Amino-terminal sequencing was then carried out on five additional samples of HB-EHM representing several of the various peaks of growth factor activity as described above. As indicated above, by SDS-polyacrylamide gel electrophoretic analysis, these samples were found to contain protein species of varying apparent molecular weights. Specifically, sample #1 (i.e., the peak eluting between the 34.5 and 43.3 minute peaks) contained a species with an apparent molecular weight of 24 kD; sample #2 (i.e., the 33 minute peak) contained a species with an apparent molecular weight of 22 kD; sample #3 (i.e., the 34.5 minute peak) contained a mixture of a species of apparent molecular weight 22 kD and a species of apparent molecular weight 19 kD; sample #4 (i.e., an independent isolation of the 34.5 minute peak) consisted primarily of a species of apparent molecular weight 19 kD; and sample #5 (i.e., the 43.3 minute peak) contained a species with an apparent molecular weight of 23 kD. An attempt to obtain the amino-terminal sequence of sample 1 was unsuccessful, indicating that this protein is amino-terminally blocked. The amino-terminal amino acid sequences obtained for Samples 2, 3, 4, and 5 were:

Sample #2 (SEQ ID NO: 4): RVXLSSKPQALAXPNKEE-HGKRKKKGKGLGKKRDPXLRKYKDFXIHGEXXY

Sample #3 (SEQ ID NO: 5): RVXLSSKPQALAXPNKEE (approx. 75% of sample) (SEQ ID NO: 6): SSKPQAL-AXXNXEE (approx. 5% of sample) (SEQ ID NO: 7): ALAXXNKXEXGKR (approx. 20% of sample)

Sample #4 (SEQ ID NO: 8): RVXLSSKPQALAXPNKEE-HGKRKK (approx. 65% of sample) (SEQ ID NO:9): XXKPQALAXXNXE (approx. 5% of sample) (SEQ ID NO: 10): ALAXPNKEEXGKR (approx. 30% of sample)

Sample #5 (SEQ ID NO:16): DLQEADLDLLRVXLXS

These amino-terminal sequencing results indicated that HB-EHM, as isolated by the purification schemes outlined in the examples above, can have several forms which differ in their amino termini. These include: a form with the originally identified amino-terminus (see SEQ ID NO:3) (VXLSSKPQALA . . . ); a form with a terminus extended one amino acid amino-terminal to the original end (see SEQ ID NO:4) (RVXLSSKPQ . . . ); a form with a terminus extended 11 amino acids amino-terminal to the original end (see SEQ ID NO:16); a form lacking the first three residues of the original form (see SEQ ID NO:6) (SSKPQALA . . . ); and a form missing the first eight residues of the original form (see SEQ ID NO:7 and 10) (ALAXPNKE . . . ). In addition, the observation that the largest (24 kD) species is amino-terminally blocked suggests that a form of HB-EHM may exist that is extended amino-terminally from the sequence (see SEQ ID NO:16) DLQEADLDLLRV.

To obtain internal amino acid sequence information, aliquots of samples 2, 3, and 4 were combined and subjected to trypsin digestion in order to generate peptide fragments for sequencing. For this analysis, the combined samples were dried, resuspended in 200 µl of 6M guanidine-HCl/ 0.5M Tris-HCl, pH 8.0/1 mM EDTA/10 mM dithiothreitol, and incubated for 60 minutes at 37° C. Iodoacetamide (0.925 mg) was added to a final concentration of 25 mM, and the solution was incubated at room temperature for 30 minutes. These two treatments were carried out to reduce and alkylate the cysteine residues in the protein. To modify lysine residues, succinic anhydride (100 mg/ml in acetonitrile) was added in four 5 µl aliquots, with a five minute incubation at room temperature between each addition. The protein mixture was desalted by passage through a $C_4$-reversed phase HPLC column, dried, resuspended in 200 µl of 100 mM ammonium bicarbonate, and digested with 0.5 µg of trypsin at 25° C. for four hours. A second aliquot of trypsin (0.3 µg) was added, and the reaction was incubated for two additional hours at 27° C. Digestion products were separated on a $C_{18}$-reversed phase HPLC (RP-HPLC) column and subjected to amino terminal sequencing.

The sequencing results indicated that the succinic anhydride treatment gave only a partial blockage of the lysine residues in the combined HB-EHM sample. Many of the fractions collected from the $C_{18}$ RP-HPLC column contained a mixture of peptide fragments. The amino acid sequences determined and the peptide residues as designated in SEQ ID NO:2 were:

| Fraction | Sequence(s) | Peptide Residues |
|---|---|---|
| J | YVKELR | 123 to 128 |
|   | DFCIHGECK | 114 to 122 |
| S | KYKDFCIHGECKYVK | 111 to 125 |
| W | DFCIHGECKYVKELR | 114 to 128 |
|   | KYKDFCIHGECKYVKELR | 111 to 128 |
| Q | KYKDFCIHGECK | 111 to 122 |
| X | KYKDFCIHGECKYVKELR | 111 to 128 |
| T | CHGLS | 143 to 147 |
|   | KYKDFCIHGECKYVK | 111 to 125 |

Additional amino acid sequence information was obtained by generating and sequencing tryptic fragments from the peak of HB-EHM activity eluting from the $C_4$ column at 47.8 minutes. A total of about 4 µg of the 47.8 minute peak material was dried and resuspended in 150 µl of 4M guanidine-HCl, 0.1M Tris-HCl, pH 8.0. Dithiothreitol (DTT) was added to a final concentration of 20 mM, and the reaction was incubated at 37° C. for 60 minutes. The reduced cysteines were then alkylated by the addition of solid iodoacetamide to a final concentration of 25 mM followed by incubation of the reaction mixture for 30 minutes at room temperature. After desalting on a $C_{18}$ reversed phase HPLC column (4.6×150 mm, Vydac; gradient of 10% to 40% acetonitrile in 0.1% trifluoroacetic acid), the protein was dried and resuspended in 150 µl of 0.1M ammonium bicarbonate. Trypsin (4 µg, Boehringer Mannheim) was added, and the reaction was incubated at 27° C. for 2 hours. The digestion products were then fractionated on the $C_{18}$ HPLC (4.6×150 mm) column using a gradient of 3% to 63% acetonitrile in 0.1% trifluoroacetic acid. All of the peaks of any appreciable absorbance (at a detection wavelength of 214 nM) were collected and subjected to sequence analysis. The amino acid sequences determined and the peptide residues as designated in SEQ ID NO:1 were:

| Fraction | Amino Acid Sequence | Peptide Residues |
|---|---|---|
| 5 | KRDPCLR | 104–110 |
| 6 | RDPCLR | 105–110 |
| 8 | APSCICHPGYHGE . . . | 129–141 |
| 10 | DFCIHGECK | 114–122 |
| 11 | KYKDFCI . . . | 111–117 |
| 12 | YKDFCIHGECK | 112–122 |
| 14 | CHGLSL . . . | 143–148 |
| 17 | DLQEADLDLLXV . . . | 63–74 |
| 18 | DLQEADLDL . . . | 63–71 |

The dots indicate that the full extent of the peptide sequence was not determined.

The most amino-terminal fragments obtained were initiated at aspartic acid residue 63; however, since this residue occurs directly after a potential trypsin cleavage site (i.e., carboxy-terminal to the arginine residue at position 62), it was not possible to conclude from this data that residue 63 necessarily represents the absolute amino-terminus of HB-EHM. The most carboxy-terminal tryptic fragment obtained extended at least through residue 148 (Leu) of the predicted precursor. Thus, the tryptic fragment sequences indicate that a mature form of HB-EHM protein exists that extends over at least 86 amino acids.

Further characterization studies were carried out on HB-EHM of amino-terminal sequence RVXLSSKPQAL-AXPNKEEHGKRKK (i.e., the form contained in the 33 minute peak) which is the predominant form in U-937 cell conditioned medium and therefore most available for structural analysis. The isoelectric points of HB-EGF and EGF were determined by chromatofocusing (as generally described in Fagerstam et al., 266 *J. Chromatogr.* 523, 1983). Briefly, 100 ng of the 33 minute peak form of HB-EHM (as described above) was applied to a Mono P column after equilibration of the column with 25 mM ethanolamine-acetic acid buffer, pH 9.4. The column was washed with this buffer for 20 minutes and subsequently with 0.1× Polybuffer 96-acetic acid, pH 6.0 (Pharmacia) for 40 minutes at a flow rate of 1 ml/min. For comparison, the isoelectric point of human recombinant EGF (Collaborative Research, Bedford, Mass.) was also determined. 100 ng of EGF was applied to a Mono P column after equilibration of the column with 25 mM imidazole-HCl buffer, pH 7.4. The column was washed with this buffer for 20 minutes and subsequently for 40 minutes with 0.125× Polybuffer 74-HCl (Pharmacia), pH 4.0 at a flow rate of 1 ml/min. Fractions of 1 ml were collected and 5 $\mu$l of each fraction were tested for growth factor activity. The pI of the 33 minute peak form of HB-EHM was found to be between 7.2 and 7.8, compared to the pI of EGF which was 5.3–5.5.

HB-EHM may be post-translationally modified. Recombinant HB-EHM produced in *E. coli* appears to be about 5–6 kDa smaller than native HB-EHM as judged by 15% polyacrylamide/SDS gel electrophoresis, and there are two threonine residues predicted from the nucleotide sequence that did not appear in protein sequencing (suggesting that these threonine residues might be sites of post-translational modification). Since threonine is a site for O-glycosylation, purified $^{125}$I-HB-EHM (i.e., the 33 minute peak described above) was produced and tested for the presence of O-linked glycosylation by treatment with endo-N-acetylgalactosaminidase (O-glycanase) as follows.

Two $\mu$g of HB-EHM were radiolabeled with Na$^{125}$I (200 $\mu$Ci/2 $\mu$l; ICN, Costa Mesa, Calif.) using Iodo-Beads (Pierce, Rockford, Ill.) by the method described in 125 *Analytical Biochem.* 427, 1982. Briefly, the iodo-beads were washed with 50 mM Tris-HCl (pH 7.4), dried, and added to a microfuge tube containing 200 $\mu$l 50 mM Tris-HCl (pH 7.4) and 200 $\mu$Ci $^{125}$I. After a 5 minute incubation HB-EHM (2 $\mu$g in 50 $\mu$l Tris-HCl, pH 7.4) was added. After a radioiodination period of 15 minutes, the reaction mixture was applied to a small heparin-Sepharose column (50 $\mu$l) equilibrated with 50 mM Tris-HCl (pH 7.4), 0.5% BSA, 200 mM NaCl, 10 mM KI. The column was washed extensively with this buffer and $^{125}$I-HB-EHM was eluted with the equilibration buffer containing 2M NaCl. The specific activity of $^{125}$I-HB-EHM was 22,500 CPM/ng. For the removal of O-linked oligosaccharide chains from $^{125}$I-HB-EHM, the $^{125}$I-HB-EHM (0.5 ng in 10 $\mu$l 50 mM Na Cacodylate, pH 6.0, 25 mM CaCl$_2$, 0.1% SDS and 10 mM DTT) was boiled for 5 minutes. The reaction mixture was adjusted to 1% Triton X-100 and 2 mM phenylmethylsulfonylfluoride (PMSF), and the sample was digested first with neuraminidase (0.01 units, Calbiochem) for 60 minutes at 37° C. and then with endo-N-acetylgalactosaminidase (0.25 milliunits; Genzyme, Cambridge, Mass.) at 37° C. overnight. The sample was analyzed by SDS/polyacrylamide gel electrophoresis. The polyacrylamide gel was dried and exposed to Kodak X-Omat autoradiography film for 12 hours at –70° C.

Treatment with O-glycanase lowered the apparent molecular weight of HB-EHM from 18–20 kDa to about 14–16 kDa (as judged by polyacrylamide gel electrophoreses) suggesting that this polypeptide was modified extensively by O-linked glycosylation.

Cloning

To isolate clones encoding HB-EHM, a cDNA library constructed from the mRNA of the human histiocytic lymphoma cell line U-937 was screened with an oligonucleotide probe, the design of which was based on the above described HB-EHM amino acid sequence [SEQ ID NO:3: VXLSSKPQALAXPNKEEHGK]. This library, purchased from Clontech Laboratories (Palo Alto, Calif.), was produced using mRNA from U-937 cells differentiated by addition of phorbol myristate acetate (PMA) at 50 ng/ml for 3.5 days; cDNA synthesized from the mRNA was cloned into the EcoRI site of cloning vector λgt10. The number of independent recombinants was reported as 1.4×10$^6$. An aliquot of the library was introduced into host cells [i.e., *E. coli* strain NM538, hsdR(r$_k$$^-$m$_k$$^+$) supF (Frischauf et al., 170 *J. Mol. Biol.* 827, 1983, hereby incorporated by reference)] by standard techniques, and the resultant plaques were immobilized on Hybond-N$^+$nylon membranes (Amersham Corporation, Arlington Heights, Ill.) and screened, by standard techniques, using as a probe, a synthetic oligonucleotide based on the amino-terminal amino acid sequence originally derived for HB-EHM. This probe was a 45-residue "codon-choice" oligonucleotide, designed by assuming that the codons encoding each of the amino acids 6 through 20 in the HB-EHM gene corresponded to the codon most commonly used for that amino acid in human genes (excluding the interferons and collagen) reported in the literature and databases (The codon frequency table used in designing the probe was generated at California Biotechnology Inc., Mountain View, Calif., by Dr. Barry Greenberg). For proline and glycine, two possible codon choices were incorporated into the probe to increase the likelihood that a correct choice would be present. In addition, CAT was used as the histidine codon at position 18, rather than the more common CAC, in order to eliminate the dinucleotide sequence CpG which is often disfavored in mammalian genes (see, e.g., Bird, 8 *Nucl. Acids Res.* 1499, 1980). The resultant 8-fold degenerate probe (probe 4955), synthesized as the antisense of the predicted coding region, was of the following sequence

```
5'  -CTTGCCATGCTCCTCCTTGTTAGGCTTGGCCAGGGCCTGAGGCTT-  3'
            T                  G                G
```

For use in screening the U-937 cDNA library filters, probe 4955 was 5' end-labelled with γ-[$^{32}$P]-ATP (Amersham Corporation, Arlington Heights, Ill.). Radioactive-labelling of the probe and filter hybridization were carried out by standard techniques; hybridization conditions included 1.7× 10$^8$ cpm of probe, a hybridization temperature of 42° C., and 200 ml of hybridization mixture (20% formamide, 6× SSC, 50 mM sodium phosphate pH 6.8, 100 µg/ml autoclaved DNA, and 5× Denhardt's solution). Following an overnight hybridization, filters were rinsed briefly three times with 1× SSC containing 0.1% sodium dodecyl sulfate (SDS). Filters were then washed twice for 30 minutes with shaking at room temperature in 1× SSC/0.1% SDS. To remove weakly-hybridizing probe molecules, the filters were washed in 1× SSC/0.1% SDS at 43–46° C. for 20 minutes in a shaking water bath. Filters were then exposed, at below −70° C., to X-ray film between two intensifying screens.

Sixteen strongly-hybridizing plaques were detected and were purified using standard techniques. Phage DNA from several of these plaques was purified as described by Sambrook et al. (*Molecular Cloning: A Laboratory Manual*, second edition, Cold Spring Harbor Laboratory Press, Cold Spring Harbor, N.Y., 1989); restriction digest analysis with EcoRI indicated that the various isolated phage contained cDNA inserts ranging in size from about 1.1 kb to 3 kb.

The insert in one such phage, λU2, was chosen for complete nucleotide sequence analysis. Fragments of this cDNA insert were ligated into appropriately-digested M13mp phages according to standard techniques, and were sequenced using the Sanger dideoxy method (Sanger et al., 143 *J. Mol. Biol.* 161, 1980). This sequence is presented in FIG. 3.

Referring to FIG. 3 (SEQ ID NO:1), nucleotides 481–540 encode an amino acid sequence that matches the initial amino-terminal HB-EHM sequence determined [SEQ ID NO:3: VXLSSKPQALAXPNKEEHGK]. The nucleotide sequence predicts a threonine residue at the second and twelfth amino acid positions, where no clear residue was detected by standard automated protein sequencing techniques in any of the HB-EHM samples analyzed. It is therefore possible that the threonines corresponding to positions 2 and 12 of the form of HB-EHM originally sequenced are modified in mature HB-EHM, possibly by O-linked glycosylation.

The coding sequence for HB-EHM lies in an open reading frame extended between the TGA termination codons at nucleotides 73–75 and nucleotides 886–888 (FIG. 3, SEQ ID NO:1). Within this open reading frame the ATG (methionine) codon at nucleotides 262–264 represents the most likely site of translation initiation, since it is the only ATG in the sequence lying 5' to nucleotides 481–483 (the codon for the valine which is the first amino acid of the amino-terminal sequence originally determined for HB-EHM). The sequence from nucleotides 253 to 265 (TGCGGGACCATGA) surrounding this ATG shares homology with the consensus sequence for vertebrate translation initiation sites (SEQ ID NO:12) [(GCC) GCCA/GCC ATG G; Kozak, 15 *Nucl. Acids. Res.* 8125, 1987], and, in particular, contains the highly conserved A residue at position −3 from the ATG. In addition, the predicted stretch of hydrophobic amino acids encoded immediately 3' to this ATG is indicative of a secretion signal sequence (von Heijne, 133 *Eur. J. Biochem.* 17, 1983), as would be expected for the amino-terminus of the primary translation product for a secreted protein like HB-EHM. Mature HB-EHM thus appears to be synthesized as part of a 208-amino acid precursor, encoded by nucleotides 262–885 in the λU2 HB-EHM cDNA. (FIG. 3, SEQ ID NO:1).

The amino termini determined from the various purified samples of HB-EHM lie at amino acids 63, 73, 74, 77, and 82 in the predicted translation product shown in FIG. 3 (SEQ ID NO:2). The amino acid residues (i.e., residues 20–62) lying between these sites and the putative hydrophobic secretion signal on the amino terminus of the precursor protein appear to represent a "pro" sequence, cleaved off post-translationally during the formation of mature HB-EHM. However, the amino terminus of the largest protein species isolated, the 24 kD form, has not yet been determined due to a blocking modification; assuming this form is an HB-EHM derivative, it may extend amino-terminally to contain some of the amino acids lying between residues 19 and 63. No differences in activity have yet been noted between the various forms of HB-EHM.

Figure 2:
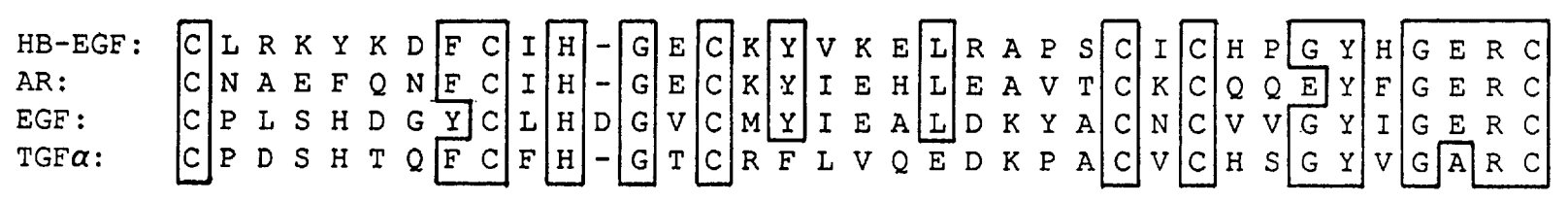

A search of the National Biomedical Research Foundation (NBRF) protein database, using the FASTA program (Pearson and Lipman, 85 *Proc. Natl. Acad. Sci. USA* 2444, 1988, Devereux et al., 12 *Nucl. Acids Res.* 387, 1984) indicated homology between HB-EHM and the EGF/TGFα/ amphiregulin family of proteins, in particular, between amino acid residues 108 and 143 (FIG. 3, SEQ ID NO:2) where HB-EHM contains all six cysteine residues conserved in the EGF (SEQ ID NO:14)/TGFα (SEQ ID NO:15)/ amphiregulin (SEQ ID NO:13) family members (FIG. 2). In the region stretching from the first to the sixth cysteine, HB-EHM conserves 40% (15 of 37) of the residues in human EGF, 42% (15 of 36) of the residues in human TGFα, and 53% (19 of 36) of the residues in human amphiregulin. Another feature shared by several of the family members is a transmembrane precursor structure that is processed amino- and carboxy-terminally to release the mature growth factor. The precursor sequence of HB-EHM shown in FIG. 3 (SEQ ID NO:2) contains a strongly hydrophobic internal domain comprising amino acids 161–184, which by analogy with the other members of the EGF/TGFα/amphiregulin family is predicted to be a transmembrane domain. The mature carboxy-terminus of HB-EHM is in turn predicted to lie between the last of the conserved cysteine residues at amino acid residue 143, and the start of the hydrophobic domain at residue 161. One of the sequenced tryptic fragments of HB-EHM consisted of the sequence CHGLS (see above). This sequence corresponds to residues 143–147 (see FIG. 3, SEQ ID NO:2). Since the sequence of this fragment ends before a tryptic cleavage site, this result is consistent with the carboxyl terminus of some forms of HB-EHM lying at amino acid residue 147. Another sequenced tryptic fragment of HB-EHM consisted of the sequence CHGLSL, corresponding to residues 143–148 (see FIG. 3, SEQ ID NO:2). The sequence data was not sufficient to show that residue 148 represents the carboxy-terminal end of the protein. Indeed, experiments with reduced and carboxymethylated synthetic peptides indicated that this tryptic fragment eluted from the $C_{18}$ RP-HPLC column at approximately the same concentration (percent) acetonitrile as does the synthetic peptide CHGLSLP. These results are consistent with residue 149 also being a carboxy-terminal end on some mature forms of HB-EHM.

Other equivalent clones can be isolated by hybridization screening techniques well known to those of ordinary skill in this art.

Binding of Heparin Binding EGF-Homologous Mitogen to EGF Receptors on A-431 Cells Because HB-EHM is structurally a member of the EGF family, it was tested for biological properties characteristic of EGF, e.g., ability to bind an EGF receptor. Competitive binding assays were used to measure this interaction and were performed as follows. [$^{125}$I]EGF (2 ng, 1.2×10$^5$ dpm, Collaborative Research, Bedford, Mass.) was added to 24 well plates containing confluent A-431 cells (Fabricant et al., 74 *Proc. Natl. Acad. Sci. USA* 565, 1977; Haigler et al., 75 *Proc. Natl. Acad. Sci. USA* 3317, 1978, available from the ATCC, Accession No. CRL 1555). Increasing amounts of HB-EHM or recombinant human EGF were then added, and the remainder of the binding assay was performed as described in Singh (147 *Meth. Enzymol.* 13, 1987, hereby incorporated by reference) and Kimball et al. (771 *Biochem. Biophys. Acta* 82, 1984, hereby incorporated by reference). Competitive [$^{125}$I]EGF binding to bovine aortic smooth muscle cells (BASMC) was measured as described above for A-431 cells, except that BASMC were used and plated in 6-well plates. Purified HB-EHM was found to bind to EGF receptors on A-431 cells and SMC. It inhibited essentially 100% of the binding of [$^{125}$I]EGF to A-431 cells as did EGF. HB-EHM had a greater affinity than EGF for EGF receptors on BASMC; HB-EHM showed a 50% inhibition of [$^{125}$I]EGF binding at 63 pg/ml (2.9 pM) compared to EGF which showed a 50% inhibition at 290 pg/ml (48 pM).

Reflecting these different affinities for the EGF receptors on BASMC, HB-EHM was found to be a more potent BASMC mitogen than EGF by the following assay. BASMC were plated in DMEM, 10% calf serum, 100 U/ml penicillin, 100 µg/ml streptomycin sulfate at 5×10$^3$ cells/well in a 24 well plate, and, after attachment of the cells (e.g., following an overnight incubation), the media was replaced with DMEM, 1% calf serum, and penicillin and streptomycin as above. HB-EHM, recombinant human EGF (Creative Biomolecules, Hopkinton, Mass.), or recombinant PDGF (Creative Biomolecules, Hopkinton, Mass.) was then added to the wells. Cells were counted after three days. The activity of HB-EHM on BASMC proliferation was more comparable to that of PDGF than to that of EGF. HB-EHM at 100 pg/ml, PDGF at 500 pg/ml, and EGF at 4 ng/ml similarly stimulated BASMC proliferation (i.e., a 2.5-fold increase).

Besides inhibiting the binding of $^{125}$I-EGF to the EGF receptor, HB-EHM (i.e., the 33 minute peak form described above) also triggered autophosphorylation of the EGF receptor. This was shown by plating A-431 cells in 6-well plates and culturing in Dulbecco's Modified Eagle's Medium (DMEM) containing 10% fetal bovine serum and antibiotics. Confluent monolayers were incubated with 5 ng/ml EGF (Collaborative Research, Waltham, Mass.) or 5 ng/ml HB-EHM. After 15 minutes, the cells were washed with ice-cold phosphate-buffered saline containing 0.4 mm EDTA, 10 mM Na-fluoride, 10 mM Na-pyrophosphate and 0.4 mM Na-orthovanadate, scraped and lysed in 100 µl of PI/RIPA buffer [1% NP-40 (Pierce, Rockford, Ill.), 1% deoxycholate (Aldrich, Milwaukee, Wis.), 0.1% SDS, 1% aprotinin (Boehringer-Mannheim, Indianapolis, Ind.), 1 mM PMSF (Pierce), 2 mM EDTA (Sigma), 10 mM Na-fluorate, (Sigma, St. Louis, Mo.), 10 mM Na-pyrophosphate (Baker, Phillipsburg, N.J.), 0.4 mM Na-orthovanadate, (Aldrich), 10 mM iodoacetamide (Aldrich) in phosphate buffered saline]. Thirty µl of supernatant clarified by spinning for a 5 minute period in a microfuge was analyzed by reducing SDS/polyacrylamide gel electrophoresis (6% polyacrylamide gel). After transfer to a nitrocellulose membrane (Schleicher and Schuell, Keen, N.H.), EGF receptor phosphorylated on tyrosine residues was detected by Western blot analysis using anti-phosphotyrosine antibodies (PY-20, ICN Biomedicals, Costa Mesa, Calif.) and subsequent development with alkaline phosphatase-conjugated rabbit antimouse IgG antibodies (Promega, Madison, Wis.) as previously described (Wada et al., 61 *Cell* 1339, 1990). A standard of phosphorylated EGF receptor was purchased from UBI (Lake Placid, N.Y.).

HB-EHM stimulated phosphorylation of a 170 kDa protein that co-migrated with an EGF receptor standard and which was also phosphorylated when cells were stimulated by EGF.

Mammalian Expression Vectors

For expression of HB-EHM in mammalian cells, the HB-EHM coding region from cDNA clone λU2 was inserted into two different expression vectors, pMTN and pAXneoR.

The vector PMTN consists of (i) a HindIII fragment of SV40 that spans the enhancer region of this virus, (ii) a HindIII-BamHI fragment spanning the promoter region of the human metallothionein II$_A$ gene, (iii) a BamHI site for insertion of the coding region to be expressed, (iv) a BamHI-EcoRI fragment spanning the 3' untranslated region of the human growth hormone gene (to provide a polyadenylation signal), (v) an EcoRI-HindIII fragment containing all of the bacterial plasmid pUC8 (except for a portion of the polylinker) to provide a bacterial origin of replication and the ampicillin resistance gene, and (vi) a fragment containing the SV40 origin of replication, and encoding resistance to neomycin and its analog, G418. This vector was constructed by first digesting the vector pMTpn (Greene et al., 231 *Science* 1150, 1986, hereby incorporated by reference) with SmaI, adding BamHI linkers, digesting with BamHI, and religating the plasmid, to create the vector pMTSV40polyA-Bam. Two fragments were then isolated from the vector pSV2-neo (Southern and Berg, 1 *J. Mol. Appl. Genet.* 327, 1982, hereby incorporated by reference): the PvuII-HindIII fragment containing the SV40 early region promoter; and the HindIII-BamHI fragment containing the neomycin resistance coding region. These two fragments were ligated together, and then treated with Klenow-fragment DNA polymerase I to produce blunt ends. The resulting DNA fragment was then ligated into the vector pMTSV40polyA-Bam, which had been partially digested with HindIII and treated with Klenow-fragment DNA polymerase I to produce blunt ends.

The vector pAXneoR consists of: (i) the 4.3 kb EcoRI-AluI fragment of the human β-actin gene isolate p14Tβ-17 containing the β-actin gene promoter (Leavitt et al., 4 *Mol. Cell. Biol.* 1961, 1984, hereby incorporated by reference; Ng et al., 5 *Mol. Cell. Biol.* 2720, 1985, hereby incorporated by reference); (ii) a short polylinker region for insertion of the coding region to be expressed; (iii) a 2.3 kb fragment, derived from the plasmid pcDV1 (Okayama and Berg, 3 *Mol. Cell. Biol.* 280, 1983, hereby incorporated by reference), containing the late region polyadenylation signal from the SV40 virus, as well as the pBR322 ampicillin resistance gene and bacterial origin of replication; and (iv) the 3.4 kb PvuII-EcoRI fragment from pSV2-neo (Southern and Berg, 1 *J. Mol. Appl. Genet.* 327, 1982, hereby incorporated by reference) containing the SV40 early promoter region (and origin of replication) linked to the bacterial neomycin resistance coding region.

For insertion into the expression vectors, the cDNA insert in clone λU2 was digested with TaqI and XmnI, releasing a fragment extending from nucleotide 219 to 970 (SEQ ID NO:1), and treated with Klenow-fragment DNA polymerase I to produce blunt ends. BamHI linkers were ligated to the resulting fragments. After digestion with BamnHI, the ligation products were fractionated on an agarose gel, and the 761 bp linkered fragment (SEQ ID NO:1) spanning the HB-EHM coding region was isolated. Ligation of this fragment into the BamHI sites of the vectors pMTN and pAX-neoR (in the orientation such that the HB-EHM coding region was operably linked to the metallothionein or actin promoter) resulted in the plasmids pMTN-HBEGF and pAX-HBEGF. The fragment of DNA containing the HB-EHM coding region may be isolated from these plasmids by digesting either pMTN-HBEGF or pAX-HBEGF with BamHI and isolating the 761 bp fragment. This fragment can then be inserted into any appropriate expression vector.

The cDNA expression plasmids, pMTN-HBEGF and pAX-HBEGF have been deposited with the American Type Culture Collection in Rockville, Md., on Sep. 25, 1990, and they, respectively, bear the accession numbers: ATCC No. 40900 and No. 40899. Applicant's assignee, The Children's Medical Center Corporation, acknowledge their responsibility to replace these cultures should they die before the end of the term of a patent issued hereon, and their responsibility to notify the ATCC of the issuance of such a patent, at which time the deposits will be made available to the public. Until that time, the deposits will be made available to the Commissioner of Patents under the terms of 37 CFR §1.14 and 35 USC §112.

Host cells used for the recombinant expression of HB-EHM were Chinese Hamster Ovary (CHO-K1) cells, obtained from the American Type Culture Collection (Accession No. CCL 61). These cells were grown at 37° C. in a 5% $CO_2$ humidified incubator in CHO growth medium [1:1 mixture of Dulbecco's Modified Eagle's Medium (DMEM-21): Coon's F12, supplemented with 10% fetal bovine serum, 2 mM L-glutamine, 50 units/ml of penicillin, and 50 µg/ml of streptomycin]. Approximately 24 hours prior to transfection with the HB-EHM expression plasmids, CHO-K1 cells were plated in 10-cm tissue culture dishes at a density of 2–3×$10^5$ cells/dish. Plasmid DNA (20 µg) was introduced into the CHO cells using the calcium phosphate precipitation method described in Wigler et al. (16 Cell 777, 1979). Four to five hours after DNA addition, the medium was aspirated from each dish and cells were "shocked" by treatment for one minute with 3 ml of 15% glycerol in HEPES-buffered saline. The glycerol was removed, the cells in each dish were rinsed with 8 ml of serum-free medium (CHO growth medium lacking 10% fetal bovine serum), and 8 ml of CHO growth medium was added to each plate. Cells were incubated for 24 hours.

For "transient" expression experiments, the medium was replaced, after the 24 hour incubation, with 5 ml of serum-free medium. In the case of cells transfected with pMTN-HBEGF or the pMTN parental plasmid, the serum-free medium was supplemented with 50 µM $ZnSo_4$ and 1 µM dexamethasone. The cells were incubated for 36 hours. The medium was then collected and assayed for the presence of HB-EHM, using the $[^3H]$-thymidine uptake assay in Balb/c mouse 3T3 cells described above. In preliminary experiments, conditioned medium from CHO-K1 cells transiently transfected with PAX-HBEGF exhibited 20 U/ml of stimulatory activity; cells transfected with the control plasmid pAXneoR yielded 10 U/ml of activity.

For the selection of stable pools of transfected cells, G418 (Geneticin; GIBCO, Grand Island, N.Y.) was added to the dishes after the 24 hour incubation period. The final concentration of the G418 was 1.0 mg/ml. Selection for G418-resistant cells extended over a period of about 2 weeks. Cells were split as necessary and re-fed with CHO growth medium containing G418. Following establishment of stable pools, cells were switched to serum-free medium (containing $ZnSO_4$ and dexamethasone in the case of pMTN- and pMTN-HBEGF-transfected cells as described above), and incubated for 24–48 hours. The conditioned medium was collected and assayed for HB-EHM activity using the $[^3H]$-thymidine uptake assay described above.

Prokaryotic Expression Vectors

If one desires to produce HB-EHM that is not glycosylated, a DNA sequence encoding mature HB-EHM can be expressed in a prokaryotic host cell. DNA encoding for mature HB-EHM is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby faciliating recovery of the protein. Prokaryotes most frequently used are represented by various strains of E. coli; however, other microbial strains may also be used. Plasmid vectors are used which contain replication origins, selectable markers, and control sequences derived from a species compatible with the microbial host. For example, E. coli may be transformed using derivatives of pBR322, a plasmid constructed by Bolivar et al. (2 Gene 95, 1977) using fragments derived from three naturally-occurring plasmids, two isolated from species of Salmonella, and one isolated from E. coli. pBR322 contains genes for ampicillin and tetracycline resistance, and thus provides multiple selectable markers which can be either retained or destroyed in constructing the desired expression vector. Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., 198 Nature 1056, 1977) and the tryptophan (trp) promoter systems (Goeddel et al., 8 Nucl. Acids Res. 4057, 1980) as well as the lambda-derived $P_L$ promoter and N-gene ribosome binding site (Shimatake et al., 292 Nature 128, 1981).

Successful production of HB-EHM in E. coli has been achieved in two ways; through expression of the factor from the plasmid pNA28 as a fusion protein with a modified form of the chloramphenicol acetyltransferase (CAT) protein, and through expression of the factor from the plasmid pNA51 as an HB-EHM protein containing an added methionine residue at the amino-terminus (termed, Met-HB-EHM). In the case of expression using the vector pNA28, the fusion protein produced was cleaved with cyanogen bromide to release the desired HB-EHM product. In the case of expression using the vector pNA51, the Met-HB-EHM product can be used either without further truncation or following treatment with cyanogen bromide to remove the amino-terminal methionine. Various E. coli strains can be used as hosts for pNA28 and pNA51; preferred hosts include E. coli strain W3110 (American Type Culture Collection Accession Number 27325; ATCC, Rockville, Md.) for pNA28 and E. coli strain B (American Type Culture Collection Accession Number 23848; ATCC, Rockville, Md.) for pNA51.

The vector pNA28 consists of (i) an origin of replication functional in E. coli derived from the plasmid pBR322; (ii) a selectable tetracycline resistance gene also derived from pBR322; (iii) the transcription termination region of the E. coli trp operon (placed at the end of the tetracycline resistance gene to prevent transcriptional read-through into the trp promoter region); (iv) the E. coli trp operon promoter, used to drive expression of the CAT-HB-EHM fusion protein; (v) the CAT-HB-EHM fusion protein coding sequence; and (vi) the T1T2 transcription terminators from the ribosomal RNA (rrnB) locus of *E. coli* (placed at the end of the CAT-HB-EHM coding region). The CAT portion of the fusion protein encoded by pNA28 is a truncated, modified version of chloramphenicol acetyltransferase; the nucleic acid and amino acid sequence of this CAT protein is shown in FIG. 5 (SEQ ID NO: 17, 18) (amino acid residues 1–73). Amino acid residue 74 of the fusion is a methionine and represents a site for cleavage by cyanogen bromide. Residues 75–149 of the fusion protein correspond to residues 73–147 of HB-EHM (see FIG. 3; SEQ ID NO: 1).

The vector pNA51 is identical in structure to pNA28, except that the nucleotide sequence encoding the CAT-HB-EHM fusion protein has been replaced by a sequence encoding a methionine amino acid fused to residues 73–147 of HB-EHM (see FIG. 3, SEQ ID NO:2).

*E. coli* strains W3110 and B bearing the expression plasmids pNA28 and pNA51, respectively, have been deposited with the American Type Culture Collection (Rockville, Md.) Oct. 24, 1991, and they, respectively, bear the accession numbers: ATCC No. 68816 and No. 68817. Applicant's assignee, The Children's Medical Center Corporation, acknowledge their responsibility to replace these cultures should they die before the end of the term of a patent issued hereon, and their responsibility to notify the ATCC of the issuance of such a patent, at which time the deposits will be made available to the public. Until that time, the deposits will be made available to the Commissioner of Patents under the terms of 37 CFR §14 and 35 USC §112.

For expression of CAT-HB-EHM, a single colony of *E. coli* strain W3110 containing pNA28 was first used to inoculate 100 ml of supplemented minimal medium (i.e., M9 salts supplemented with 0.4% glucose, 2 μg/ml thiamine, 1% casamino acids, 0.1 mM $CaCl_2$, 0.8 mM $MgSO_4$, and 6.25 μg/ml tetracycline) containing 40 μg/ml tryptophan. The 100-ml culture was grown overnight with shaking at 37° C., and aliquots of this culture (10 ml per liter) were then used to inoculate one-liter batches of supplemented minimal medium containing 4 μg/ml tryptophan. Usually, eight one-liter batches were inoculated together on a given day. Each one-liter culture was incubated at 37° C. with shaking in a four-liter triple-baffled Erlenmeyer flask until an optical density ($OD_{600}$) of 0.5–0.7 was reached, at which point, 30 mg of 3β-indoleacrylic acid (Sigma) in 10 ml of ethanol was added to the flask to induce the trp promoter. The cultures were then incubated overnight with shaking at 37° C., and the cells were harvested by centrifugation at 4500 rpm in a Sorvall RC-3B centrifuge for 20 minutes. The cell pellets from one to eight one-liter batches were resuspended in water or TE buffer (20 mM Tris-HCl, pH 7.5, 5 mM EDTA), combined, and centrifuged to repellet the cells. The resulting washed pellet was either used directly for protein purification or was frozen at −20° for storage prior to cell lysis.

When CAT-HB-EHM was expressed as described above, the fusion protein was localized into inclusion bodies within the cells. To isolate the inclusion bodies, the fresh or frozen cell pellet obtained as described above was resuspended in TED buffer (20 mM Tris-HCl, pH 7.5, 5 mM EDTA, 1 mM DTT), placed on ice, and sonicated using a Heat Systems Ultrasonics sonicator (power level of 7; 50% pulsed cycle; 0.5 inch diameter probe; Farmingdale, N.Y.). The cells were ruptured using 2–5 two-minute sonication intervals, with a two-minute cooling period between each interval. The resulting suspension was mixed with 6M guanidine until a final concentration of 1M guanidine was reached and was then centrifuged for 10 minutes at 16,000×g (10,000 rpm, GSA rotor) to pellet the inclusion bodies. The pellet was washed by resuspension in TED buffer containing 1M guanidine, followed by re-centrifugation at 16,000×g for 10 minutes.

To cleave HB-EHM away from the CAT portion of the fusion protein, the inclusion bodies were first resuspended in 70% formic acid (8–10 ml per gram wet weight of inclusion bodies). Cyanogen bromide (50 mg per gram wet weight of inclusion bodies) was then added, and the resulting solution was overlaid with argon and stirred at room temperature for four hours. The solution was dried under vacuum, resuspended in 20 mM Tris-HCl, pH 7.5, 5 mM EDTA, 6M urea, and then centrifuged for 10 minutes at 16,000×g. The supernatant was retained, and the pellet was resuspended a second time in 20 mM Tris-HCl, pH 7.5, 5 mM EDTA, 6M urea. The resuspension was centrifuged as above at 16,000×g for 10 minutes, and the resulting supernatant was combined with the first retained supernatant.

For purification of HB-EHM from the cyanogen bromide cleavage mix, the combined supernatants were loaded onto a column of SP-Sephadex C25 (2.5 cm×2 cm, Pharmacia) that had been pre-equilibrated with 20 mM Tris-HCl, pH 7.5, 5 mM EDTA, 6M urea, 0.1M NaCl. After loading was complete, the column was washed with the equilibration buffer until the absorbance of the eluate reached baseline. Bound proteins were then eluted from the column with 20 mM Tris-HCl, pH 7.5, 5 mM EDTA, 6M urea, 0.6M NaCl. At this point, the denatured protein in the eluate was allowed to refold by (1) adding glutathione (Boehringer-Mannheim) and glutathione disulfide (Boehringer-Mannheim) to concentrations of 6 mM and 1.2 mM, respectively, (2) diluting the resulting solution with five volumes of 20 mM Tris-HCl, pH 8.8, 5 mM EDTA, and (3) letting the solution stand at 4° C. for between 4 and 24 hours. Any precipitate forming during this time was removed by centrifugation, and the protein was then loaded onto a heparin-Sepharose column (2 cm×2.5 cm, Pharmacia) equilibrated with 20 mM Tris-HCl, pH 7.5, 5 mM EDTA, 0.1M NaCl. After extensive washing with the equilibration buffer, the bound protein was step-eluted first with 20 mM Tris-HCl, pH 7.5, 5 mM EDTA, 0.6M NaCl, and then with 20 mM Tris-HCl, pH 7.5, 5 mM EDTA, 2M NaCl. Final purification of the recombinant HB-EHM was accomplished by loading the 2M elute from the heparin-Sepharose column onto a Vydac $C_4$ reversed-phase column (1 cm×25 cm) equilibrated with 15% acetonitrile in 0.1% trifluoroacetic acid, and then eluting the bound protein with a 40-minute gradient of 15% to 35% acetonitrile in 0.1% trifluoroacetic acid. Elution of the HB-EHM was monitored by measuring absorbance of the eluate at 214 nm and by SDS/polyacrylamide gel electrophoresis of aliquots of collected fractions. The HB-EHM was dried under vacuum, resuspended in phosphate-buffered saline, and shown to be active in the BALB/c 3T3 [$^3$H]-thymidine uptake assay.

For expression of Met-HB-EHM, *E. coli* strain B cells harboring pNA51 were used to inoculate M9 salts supplemented with 0.4% glucose, 1.1% casamino acids, 2 mM $Mg_2SO_4$, and 6.25 μg/ml tetracycline. The culture was grown with shaking at 30° C. until the $OD_{600}$ of the culture reached approximately 0.45, at which point 3β-indoleacrylic acid was added to a final concentration of 30 μg/ml to induce the trp promoter. The culture was incubated at 30° C. with shaking for 4 hours, and half of the culture was harvested by centrifugation. The other half of the culture was shaken at 30° C. for an additional period of about 16 hours (about 20 hours total incubation time after the addition of 3β-indoleacrylic acid) before being harvested by centrifugation. The cell pellets from the centrifugations were each resuspended to an approximate protein concentration of 10 mg/ml in 0.1M Tris-HCl, pH 8.8, 5 mM EDTA and were then sonicated to lyse the cells. The resulting solutions were centrifuged to remove cell debris, and the supernatants were retained. Since Met-HB-EHM expression was detectable by polyacrylamide gel electrophoresis in lysates of cells collected either 4 hours or 20 hours after 3β-indoleacrylic acid induction, the supernatants from these two time points were combined. The resulting supernatant solution was loaded onto a heparin-Sepharose column equilibrated with 50 mM Tris-HCl, pH 7.5, 5 mM EDTA, 0.1M NaCl. The column was washed with 5 mM Tris-HCl, pH 7.5, 5 mM EDTA, 0.6M NaCl until the eluate absorbance was reduced to background, at which point, the bound protein was eluted with 50 mM Tris-HCl, pH 7.5, 5 mM EDTA, 1.2M NaCl. The eluted protein was dialyzed overnight at 4° C. against 50 mM Tris-HCl, pH7.5, 5 mM EDTA, and then fractionated on a Vydac $C_4$ RP-HPLC column (0.46 cm×25 cm) using an elution gradient of 10%–40% acetonitrile in 0.1% trifluoroacetic acid. The major peak of protein eluting from the column (as monitored by absorbance at 220 nm) was collected and shown both to have the amino-terminal amino acid sequence expected for Met-HB-EHM, and to be active in the BALB/c 3T3 [$^3$H]-thymidine incorporation assay.

Use

Growth factors of this invention are useful for enhancing the healing of wounds. A wound healing amount of a growth factor is readily determined by one of ordinary skill in the art using standard techniques, and such an amount is applied to the wound by standard technique. Such growth factors can be used to treat many types of chronic non-healing wounds such as full-thickness dermal ulcers, for example, pressure sores, venous ulcers, and diabetic ulcers; to treat acute wounds such as burns, incisions, and injuries; and to speed the healing of wounds associated with reconstructive procedures such as skin grafting and flap placement used, for example, to repair wounds and for cosmetic purposes. In addition, such growth factors can be used to treat damage to the gastric epithelium, the lung epithelium, and other internal epithelial layers. For example, such growth factors, being resistant to extremes of pH, can be used to heal ulcers of the esophagus, stomach, duodenum, and intestine. Also, because of their epithelial cell-stimulatory activity, such growth factors can be used to treat eye injuries, for example, corneal ulcers and abrasions.

In cases where the growth factors of this invention are being used for surface wound healing, they may be administered by topical means. In these cases, they will be applied directly to the site of injury as either a solution, spray, gel, cream, ointment or as a dry powder. Slow release devices directing these growth factors to the injured site will also be used as will the combination of such growth factors with topical bandages, or dressings, or sutures/staples, and with topical creams and ointments, such as the antibacterial Silvadene (Marion Labs, Kansas City, Mo.), commonly used for the treatment of injuries.

For topical use, the growth factors of this invention will be used at a concentration ranging from 50–10,000 μg/ml either in a single application, or in dosing regimes that range from several times per day to once every few days for a period of one to several weeks. Usually, the amount of topical formulation administered is that which is sufficient to apply about 0.01 to 100 μg/cm$^2$ of growth factor per surface area of the wound. For application to injuries of the gastrointestinal tract, these growth factors will be administered orally or rectally in a suitably buffered solution that may contain a carrier compound to protect the protein from the acid pH and high protease levels encountered in the gastric tract. In addition, these growth factors may be infused via catheter directly to the site of an internal injury. For opthalmic applications, such growth factors may be used in an eye drop form or in an ointment. For lung injury, the factor may be administered by inhalation of a spray or aerosol.

Growth factors of this invention can also be used for the in vitro culturing of responsive cell types, for example, fibroblasts, smooth muscle cells, or epithelial cells. For such uses, the growth factors can be added to the cell culture medium at a concentration from 10 pg/ml to 100 ng/ml. In addition, cells grown under growth factor stimulation can be used as a source of expanded cell populations for grafting purposes. For all of these applications, the growth factors of this invention may be used alone or in combination with other growth factors and biologically active agents.

Growth factors of this invention can be used in standard protocols for production of polyclonal or monoclonal antibodies to those growth factors. Such monoclonal antibodies are useful in this invention for detection of growth factors within the serum of a patient. The amount of growth factor detected by such a procedure can be compared to the normal level of such growth factors in equivalent patients. An elevated level of such growth factors (e.g., two or three fold elevation) is indicative of that patient suffering from atherosclerosis. Such patients which suffer from atherosclerosis because of an elevated level of growth factor can be treated by reducing the level of growth factor either by adding antibodies to the growth factor directly to the serum of the patient or by release of such antibodies from a slow release device implanted, e.g., in the affected blood vessel(s). Alternatively, the level of activity or expression of the growth factor may be reduced by addition of antagonists or by use of an antisense RNA molecule (e.g., a 20 nucleotide sequence complementary to the HB-EHM mRNA in the region spanning the translational start site) incorporated into a biocompatible sustained-release polymeric device.

HB-EHM-induced proliferation of target cells (e.g., fibroblasts, epithelial cells and smooth muscle cells) provides an assay for screening candidate antagonists for ones which block the growth-stimulatory activity of a growth factor of this invention. For example, candidate antagonists would be added to cultured cells together with a growth factor of this invention and cell stimulation would be measured by [$^3$H]-thymidine incorporation into cellular DNA (as described above) or by counting the number of cells after an appropriate period of incubation (as described above). This measurement would be compared to a control cell sample incubated under identical conditions, but to which no candidate antagonist was added. Useful antagonists would be defined as those molecules which inhibit (i.e., decrease the amount of cell proliferation induced by growth factor stimulation). These antagonists, once identified, would be used to inhibit the in vivo activity of a growth factor of this invention. Antagonists may be useful, for example, in the treatment of atherosclerosis, for blocking post-angioplasty proliferation, or for the treatment of certain neoplasias or myelofibrosis. The antagonist, in this case, could be added directly to the blood of the patient, could be incorporated into a slow-release device, or if possible, could be administered topically to the affected area. Candidate antagonists may be chosen from any source and would include, without limitation, antibodies which preferentially bind to HB-EHM or its receptor, peptide fragments of HB-EHM, or identified or as yet unidentified drugs.

In addition, certain tumor cell types may be found to synthesize the growth factors of this invention. If so, the presence of HB-EHM mRNA or protein may be used as a diagnostic for the presence and/or expansion of certain tumor types. Immunoassays (e.g., Western blot or ELISA, using an antibody which recognizes a growth factor of this invention), mRNA-based assays (e.g., Northern blot, using as a probe, a nucleic acid encoding a growth factor of this invention), and other assays such as an EGF-receptor binding assay would be useful for diagnosing the presence of an HB-EHM-producing tumor and for monitoring its regression upon therapy.

Other embodiments are within the following claims.

We claim:

1. A Heparin-binding EGF-homologous Mitogen (HB-EHM) polypeptide that includes a segment comprising the entire amino acid sequence 108 to 143 of SEQ ID NO: 2, said polypeptide being characterized in that it:
   a) stimulates growth of one or more of the following types of cells: i) fibroblast cells, ii) epithelial cells, or iii) smooth muscle cells; and
   b) is either purified to homogeneity or is unglycosylated.

2. The HB-EHM polypeptide of claim 1 further characterized in that it binds to heparin.

3. The HB-EHM polypeptide of claim 1 further characterized in that it binds an EGF receptor on a fibroblast, an epithelial, or a smooth muscle cell.

4. The HB-EHM polypeptide of claim 3 further characterized in that it does not stimulate the growth of endothelial cells.

5. The HB-EHM polypeptide of claim 1, wherein the segment includes the entire portion of the amino acid sequence of SEQ ID NO: 2 starting at an amino terminus between amino acids 63 and 82 of SEQ ID NO:2 and extending to a carboxyl terminus between amino acids 147 and 149 of SEQ ID NO:2.

6. The HB-EHM polypeptide of claim 1, wherein the segment includes the entire portion of the amino acid sequence of SEQ ID NO: 2 starting at an amino terminus between amino acids 73 and 82 of SEQ ID NO:2 and extending to amino acid 147 of SEQ ID NO:2.

7. The HB-EHM polypeptide of claim 1, wherein said segment is an amino acid sequence selected from the group consisting of amino acids 63–148, amino acids 73–147, and amino acids 82–147, all of SEQ ID NO: 2.

8. The HB-EHM polypeptide of claim 1, wherein said segment comprises an amino acid sequence identical to amino acids 1–208 of SEQ ID NO: 2.

9. The HB-EHM polypeptide of claim 1, wherein said polypeptide is characterized by one of the following amino terminal sequences:
   (a) an amino acid sequence identical to amino acid residues 73–123 of SEQ ID NO:2
   (b) an amino acid sequence identical to amino acid residues 73–90 of SEQ ID NO:2;
   (c) an amino acid sequence identical to amino acid residues 77–90 of SEQ ID NO:2;
   (d) an amino acid sequence identical to amino acid residues 73–96 of SEQ ID NO:2;
   (e) an amino acid sequence identical to amino acid residues 77–89 of SEQ ID NO:2;
   (f) an amino acid sequence identical to amino acid residues 82–94 of SEQ ID NO:2; or
   (g) an amino acid sequence identical to amino acid residues 63–78 of SEQ ID NO:2.

10. A pharmaceutical composition for wound healing comprising the polypeptide of claim 1 in an effective wound healing amount and a pharmaceutically-acceptable carrier.

11. The pharmaceutical composition of claim 10, wherein said segment comprises the entire amino acid sequence 73–147 of SEQ ID NO: 2.

12. A method for healing a wound in a patient comprising applying to the wound a wound healing amount of the HB-EHM polypeptide of claim 1.

13. A method for the in vitro culturing of a cell whose growth is stimulated by HB-EHM, said method comprising contacting said cells with a growth-stimulatory amount of the HB-EHM polypeptide of claim 1.

14. The method of claim 13, wherein said cells are fibroblasts, epithelial cells, or smooth muscle cells.

15. Isolated nucleic acid which encodes a Heparin-binding EGF-homologous Mitogen (HB-EHM) polypeptide, said polypeptide including a segment comprising the entire amino acid sequence 108 to 143 of SEQ ID NO: 2, said polypeptide being characterized in that it stimulates growth of one or more of the following types of cells: i) fibroblast cells, ii) epithelial cells, or iii) smooth muscle cells.

16. A vector containing the nucleic acid of claim 15.

17. The vector of claim 16, said vector being the plasmid PMTN-HBEGF, deposited with the ATCC and designated ATCC Accession No. 40900.

18. The vector of claim 16, said vector being the plasmid pAX-HBEGF, deposited with the ATCC and designated ATCC Accession No. 40899.

19. The vector of claim 16, said vector being the plasmid pNA28, deposited with the ATCC and designated ATCC Accession No. 68816.

20. The vector of claim 16, said vector being the plasmid pNA51, deposited with the ATCC and designated ATCC Accession No. 68817.

21. A method of producing a HB-EHM polypeptide comprising the steps of:

(a) providing a cell that has been transformed with the vector of claim 16;

(b) culturing said cell under conditions which permit expression of said polypeptide; and (c) recovering said polypeptide.

22. The method of claim 21 in which said cell is a prokaryotic cell.

23. A polypeptide produced by the method of claim 22.

24. A cell which contains the nucleic acid of claim 15.

* * * * *